(12) United States Patent
Eliason

(10) Patent No.: US 11,372,620 B1
(45) Date of Patent: Jun. 28, 2022

(54) VOICE MONITORING SYSTEM AND METHOD

(71) Applicant: Jarrod Eliason, Brooklyn Park, MN (US)

(72) Inventor: Jarrod Eliason, Brooklyn Park, MN (US)

(73) Assignee: Family Tech Innovations, LLC, Brooklyn Park, MN (US)

( * ) Notice: Subject to any disclaimer, the term of this patent is extended or adjusted under 35 U.S.C. 154(b) by 0 days.

(21) Appl. No.: 17/399,459

(22) Filed: Aug. 11, 2021

(51) Int. Cl.
| G06F 3/16 | (2006.01) |
| G06F 1/16 | (2006.01) |
| G06Q 10/10 | (2012.01) |
| G06F 3/0488 | (2022.01) |
| G06F 3/01 | (2006.01) |

(52) U.S. Cl.
CPC .............. *G06F 3/167* (2013.01); *G06F 1/163* (2013.01); *G06F 3/016* (2013.01); *G06F 3/0488* (2013.01); *G06F 3/165* (2013.01); *G06Q 10/1093* (2013.01)

(58) Field of Classification Search
CPC .......... G06F 3/167; G06F 1/163; G06F 3/016; G06F 3/0488; G06F 3/165; G06Q 10/1093
See application file for complete search history.

(56) References Cited

U.S. PATENT DOCUMENTS

| 7,142,894 B2 | 11/2006 | Ichikawa et al. |
| 8,019,050 B2 * | 9/2011 | Mactavish ............... G10L 25/48 381/86 |
| 8,183,997 B1 | 5/2012 | Wong et al. |
| 8,423,368 B2 | 4/2013 | Rothenberg |
| 8,929,535 B1 | 1/2015 | Czachor, Jr. et al. |
| 9,094,514 B2 | 7/2015 | Czachor, Jr. et al. |
| 9,300,800 B2 | 3/2016 | Czachor, Jr. et al. |
| 9,336,795 B1 * | 5/2016 | Robertson ............ A61B 5/4803 |

(Continued)

OTHER PUBLICATIONS

"A Portable Voice Volume Monitor", Louisiana State University, [Online] Retrieved from the Internet: <URL: https://www.ibridgenetwork.org/#!/profiles/9025150090589/innovations/31/>, [Retrieved on Sep. 12, 2018], (2018), 2 pgs.

(Continued)

*Primary Examiner* — Fan S Tsang
*Assistant Examiner* — David Siegel
(74) *Attorney, Agent, or Firm* — Schwegman Lundberg & Woessner, P.A.

(57) ABSTRACT

An exemplary voice monitoring system includes a wearable voice monitor and an auxiliary device such as a smart phone. The wearable monitor incorporates a wake-on-sound microphone, a vibration motor, and a microcontroller within a small, discreet enclosure. The enclosure can be hung from a necklace chain or affixed to clothing, like a piece of jewelry. The jewelry appearance is enhanced by a removable decorative piece. The microcontroller wakes up in response to a wake signal from the microphone when a voice sound of a wearer is detected. The microcontroller initiates measurements to determine if the voice sound meets preconfigured criteria and activates the vibration motor to alert the wearer. Sound criteria resulting in vibratory alerts are contained in a user-specific schedule tailored according to time of day and day of week. The smart phone can remotely create customized schedules and transmit them to the monitor.

29 Claims, 21 Drawing Sheets

(56) References Cited

U.S. PATENT DOCUMENTS

| | | | |
|---|---|---|---|
| 9,532,633 B1* | 1/2017 | Tan | B44C 5/00 |
| 9,936,900 B2 | 4/2018 | Chang et al. | |
| 9,940,811 B2 | 4/2018 | Chang et al. | |
| 2009/0180623 A1 | 7/2009 | Frohlich et al. | |
| 2009/0180631 A1 | 7/2009 | Michael et al. | |
| 2011/0236577 A1* | 9/2011 | Law | B41M 3/06 |
| | | | 427/256 |
| 2015/0110277 A1 | 4/2015 | Pidgeon et al. | |
| 2015/0110279 A1 | 4/2015 | Tejerina | |
| 2017/0221336 A1* | 8/2017 | Ogaz | G10L 25/66 |
| 2018/0315441 A1* | 11/2018 | Sapienza | G09B 19/04 |
| 2020/0204899 A1* | 6/2020 | Moudgill | H04R 1/1016 |
| 2021/0117680 A1* | 4/2021 | Chaudhri | G06F 1/1686 |

OTHER PUBLICATIONS

"Ambulatory Phonation Monitor (APM)", Somnotec, [Online] Retrieved from the Internet: <URL: http://www.somnotec.net/portfolio-items/arnbulatory-phonation-monitor-apm/>, [Retrieved on Sep. 12, 2018], (2016), 2 pgs.

"U.S. Appl. No. 14/461,411, Non-Final Office Action dated Mar. 8, 2016", 12 pgs.

"Instruction Manual for VocaLog 2™ Vocal Activity Monitor", VocaLog2 Help file, [Online] Retrieved from the Internet: <URL: http://www.vocalog.com/VL2_Help/VocaLog2_Help.html>, [Retrieved on Aug. 13, 2021], (2014), 16 pgs.

"Voice Ruler sound level meter", ZYGO-USA, [Online] Retrieved from the Internet: <URL: https://www.zygo-usa.com/usa/index.php/our-products/assistive-technologies-at/aids-to-daily-living/voice-ruler-sound-level-meter>, [Retrieved on Sep. 12, 2018], (2011), 4 pgs.

Hillman, Robert E, "Improving the Assessment and Treatment of Voice Disorders: Emerging Technologies", Proceedings of From Sound to Sense 2004, MIT, (Jun. 11-13, 2004), B-173-B-178.

Mehta, Daryush D, et al., "Mobile Voice Health Monitoring Using a Wearable Accelerometer Sensor and a Smartphone Platform", IEEE Transactions on Biomedical Engineering, 59(11), (Nov. 2012), 3090-3096.

Van Stan, Jarrad H, et al., "Direct Comparison of Three Commercially Available Devices for Voice Ambulatory Monitoring and Biofeedback", Perspectives on Voice and Voice Disorders, 24(2), 80-86, (Jul. 2014), 8 pgs.

Van Stan, Jarrad H, et al., "The Effect of Voice Ambulatory Biofeedback on the Daily Performance and Retention of a Modified Vocal Motor Behavior in Participants With Normal Voices", Journal of Speech, Language, and Hearing Research, 58(3), (Jun. 2015), 713-721.

\* cited by examiner

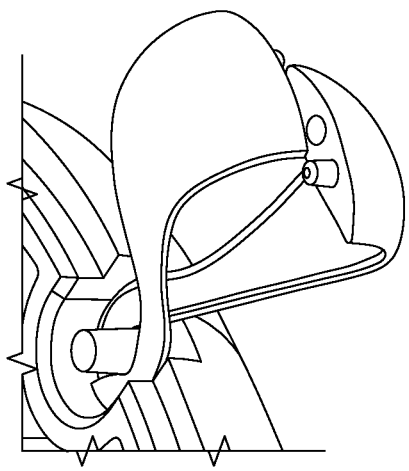
FIG. 24A
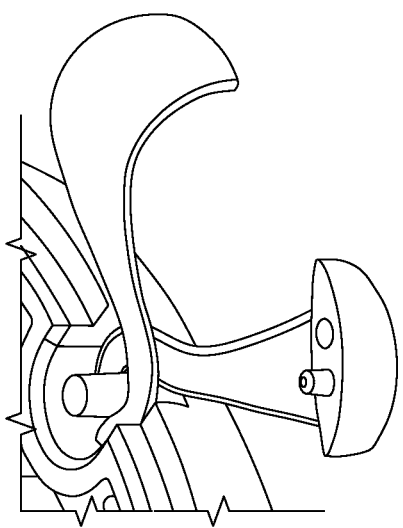
FIG. 24B
FIG. 24C
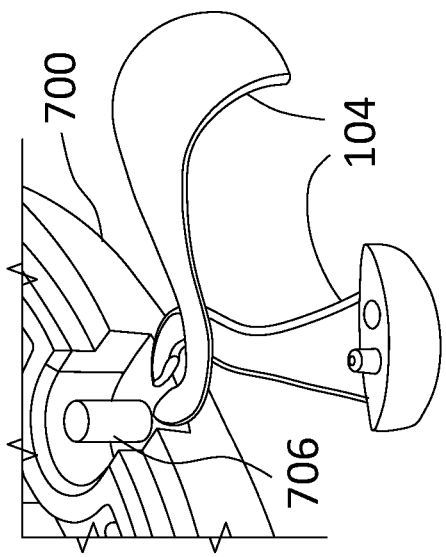
FIG. 24D
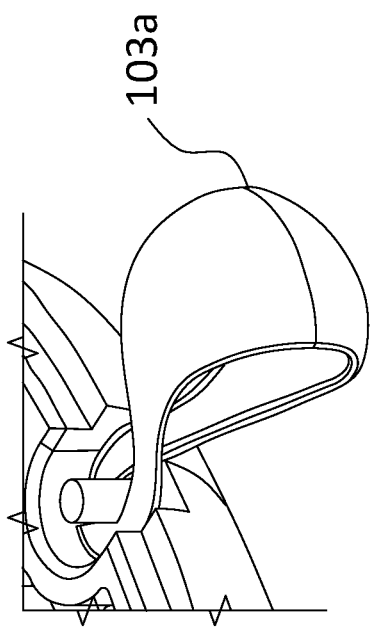
FIG. 24E

VOICE MONITORING SYSTEM AND METHOD

TECHNICAL FIELD

The present disclosure relates to a wearable electronic biofeedback device usable in conjunction with a separate electronic device such as a smart phone. In particular, but not by way of limitation, the present disclosure relates to a wearable electronic biofeedback device that can take the form of a necklace or pendant, which can vibrate when the wearer speaks at a volume that is above or below specified maximum or minimum thresholds.

BACKGROUND

As of 2019, Autism Spectrum Disorder (ASD) affected 1 in 59 children in the United States, and the rate of ASD is increasing. One behavior present in many people with ASD is overly loud talking, which is especially noticeable in socially inappropriate locations or circumstances.

BRIEF SUMMARY

An approach that can help people with ASD with overly loud talking can include using electronic devices that can indicate when volume is too loud, such as with a software application that can allow a smart phone or smart watch to perform volume monitoring and feedback. Such an approach can be effective at limiting voice volume when such a device is worn, but the change in voice volume may not persist when device usage is stopped. The present inventor has recognized, among other things, that it may be helpful to provide a discreet voice volume monitor that can be worn consistently.

To meet this goal, certain challenges can be addressed. For example, smart phone and smart watch microphones can pick up sound from the environment that can lead to false triggers. Additionally, smart phones are expensive, and parents may not be comfortable giving them to children with ASD. Devices built specifically for voice monitoring, which can be referred to as ambulatory phonation monitors, can help overcome the environmental sound problem by attaching a sound transducer (microphone or accelerometer) to the user's neck with surgical tape or other adhesive. While effective, such an approach can involve devices that can have an unsightly cable running between the transducer and the device electronics, which is mounted on the back of the neck or clipped to a belt.

The mounting location of the electronics used in certain ambulatory phonation monitors is limited by their size, which is primarily driven by the size of the battery needed to power the device throughout the day. With available rechargeable battery technology, a pendant-sized device is limited to around 370 milliwatt-hours (3.7V×100 mA-hour) energy usage. To support all-day use (16 hours) on a single charge, the average power consumption of such a device must be below 23 milliwatts. A device with even lower average power consumption would enable the device to be smaller and lighter, and/or enable a longer operating time between charges.

Small devices are easy to misplace, and jewelry is often lost. Smart phones can include a "find my device" feature that generates a noise in response to a request via a wireless interface. Small Bluetooth® Low-Energy devices, often referred to as tiles, can extend this feature to a variety of commonly lost items such as car keys.

Socially appropriate voice levels can vary widely across location and situations. Take, for example, the case of a student attending public school. In the morning, at breakfast with his family, he is expected to speak at moderate indoor levels. Later, on his bus ride to school, voice levels rise as several simultaneous conversations raise the background level. Once class starts, he is again expected to speak quietly during instruction, but voice volumes may increase as he moves between classes during passing periods or speaks with friends in the lunchroom. Some classes, such as music classes, may involve significantly higher sound levels. Some activities, such as theater performance, may encourage loud speech. Certain approaches to ambulatory phonation monitors do not support threshold scheduling to account for the wide range of environments and situations a wearer may encounter throughout the day. Similar wearable biofeedback devices can be used for posture monitoring. However, desirable posture angles do not change over time, so these devices do not offer time-based threshold schedules.

Use of a wearable device such as an ambulatory phonation monitor requires cooperation from the wearer. Overly large or obvious devices may cause the wearer to be self-conscious and choose not to wear the device. Some wearable devices can be disguised as pieces of jewelry, but preferred styles of jewelry are highly subjective. A particular wearable device may not satisfy a wide range of fashion sensibilities, may not provide choices for the decorative features of the device, and may not provide wearers the option to remove and change decorative pieces.

The present inventor has recognized, among other things, that what is needed is a small, discreet wearable voice monitor that can be programmed to change voice volume thresholds according to a schedule; and that can change appearance to accommodate the stylistic tastes of the wearer.

The present approach can help offer certain advantages, such as by mounting the sound transducer and all the electronics within a small, discreet enclosure that can be hung from a necklace chain or affixed to clothing such that it appears to be a piece of jewelry. The jewelry appearance can be further enhanced by removable decorative pieces.

Wake-on-sound microphone technology can allow the present approach to minimize energy usage by remaining in a low-power sleep mode until a sound exceeding the wake threshold of a wake-on-sound microphone is detected. A microcontroller can wake up in response to the wake signal and can initiate a sequence of measurements such as to determine if the sound meets one or more established criteria for vibration motor activation or actuation to alert the user.

A measurement of voice volume can involve activating a logarithmic amplifier or amplitude conversion circuit, sampling a sound signal through an analog-to-digital converter, and applying a digital filtering algorithm to make the monitor less susceptible to false triggers from non-vocal sound impulses. To extend operation time per battery charge, the microcontroller, wake-on-sound microphone and logarithmic amplitude conversion circuit can be returned to a sleep state in between a series of samples triggered by the wake-on-sound event.

User-specific threshold schedules can allow for the thresholds triggering alerting vibration motor activation to change throughout the day and throughout the week. A user-interface on a separate scheduling device, such as a smart phone, can facilitate creation of customized schedules. The user-interface can also allow retrieval of data logs from the wearable device.

BRIEF DESCRIPTION OF THE DRAWINGS

FIGS. 24A-24E are perspective views of two bail halves and the bail post at various stages of the attachment process.

DETAILED DESCRIPTION

Figure 1:
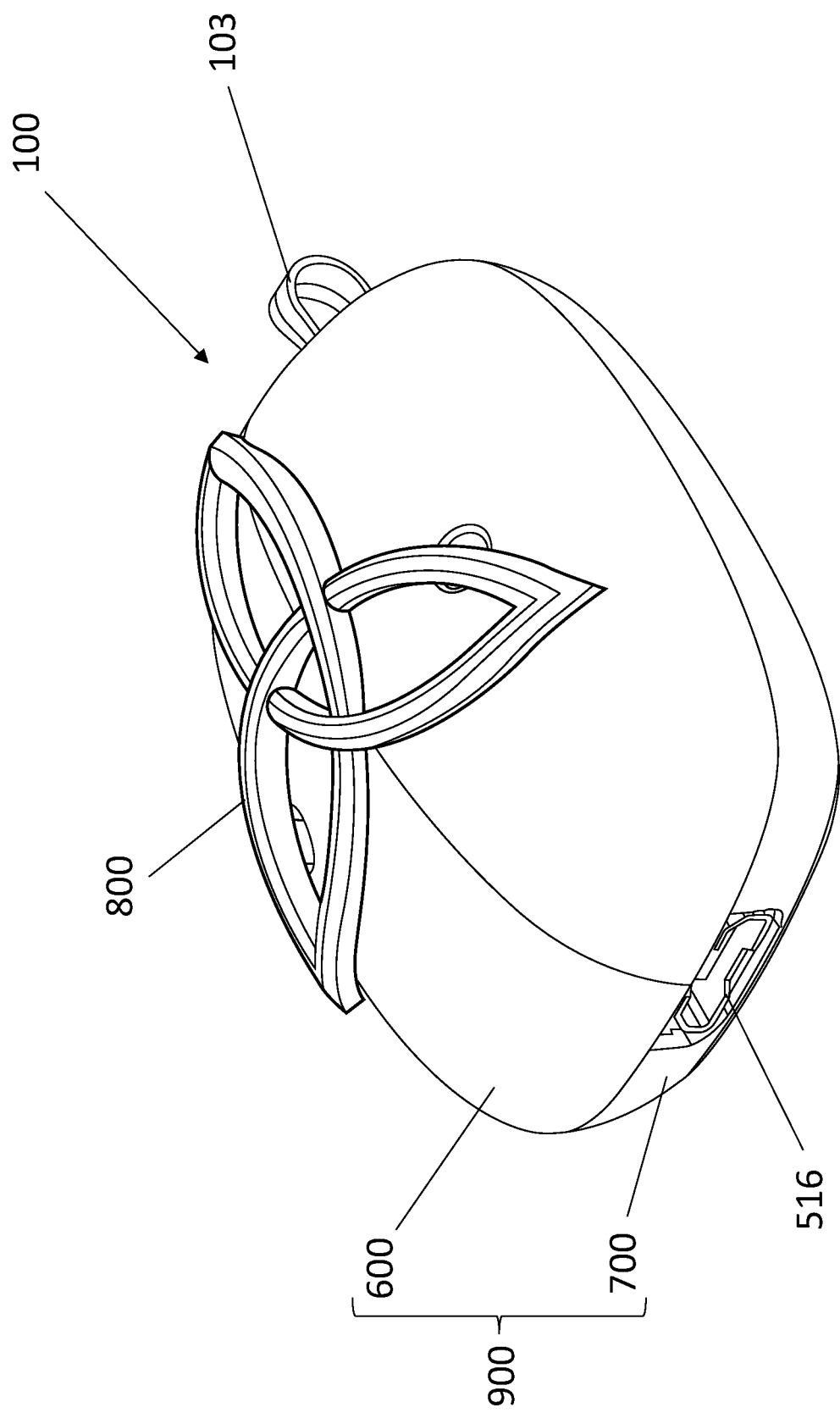
FIG. 1 is an example of a perspective view of portions of a wearable voice volume monitor with a decorative piece.

A voice monitoring system can include a wearable device, such as a wearable voice monitor 100, such as illustrated in the example of FIG. 1. Electronics of the monitor 100 can be housed within a receptacle within a two-part enclosure 900 such as having a top housing 600 and a bottom housing 700. The top and bottom housings 600, 700 can be fitted together to form the enclosure 900. For example, the top and bottom housings 600, 700 can be glued together at a joint therebetween. A pendant bail 103 can be included, such as can serve as an attachment point such as for hanging therefrom a flexible strand such as a necklace chain, string, or lanyard for example. A user-attachable and user-detachable decorative piece 800 can be user-attached to and user-detached from the enclosure 900, using at least one first receiving fixture, such as holes 601A, 601B in the top housing 600 (see below).

Figure 2:
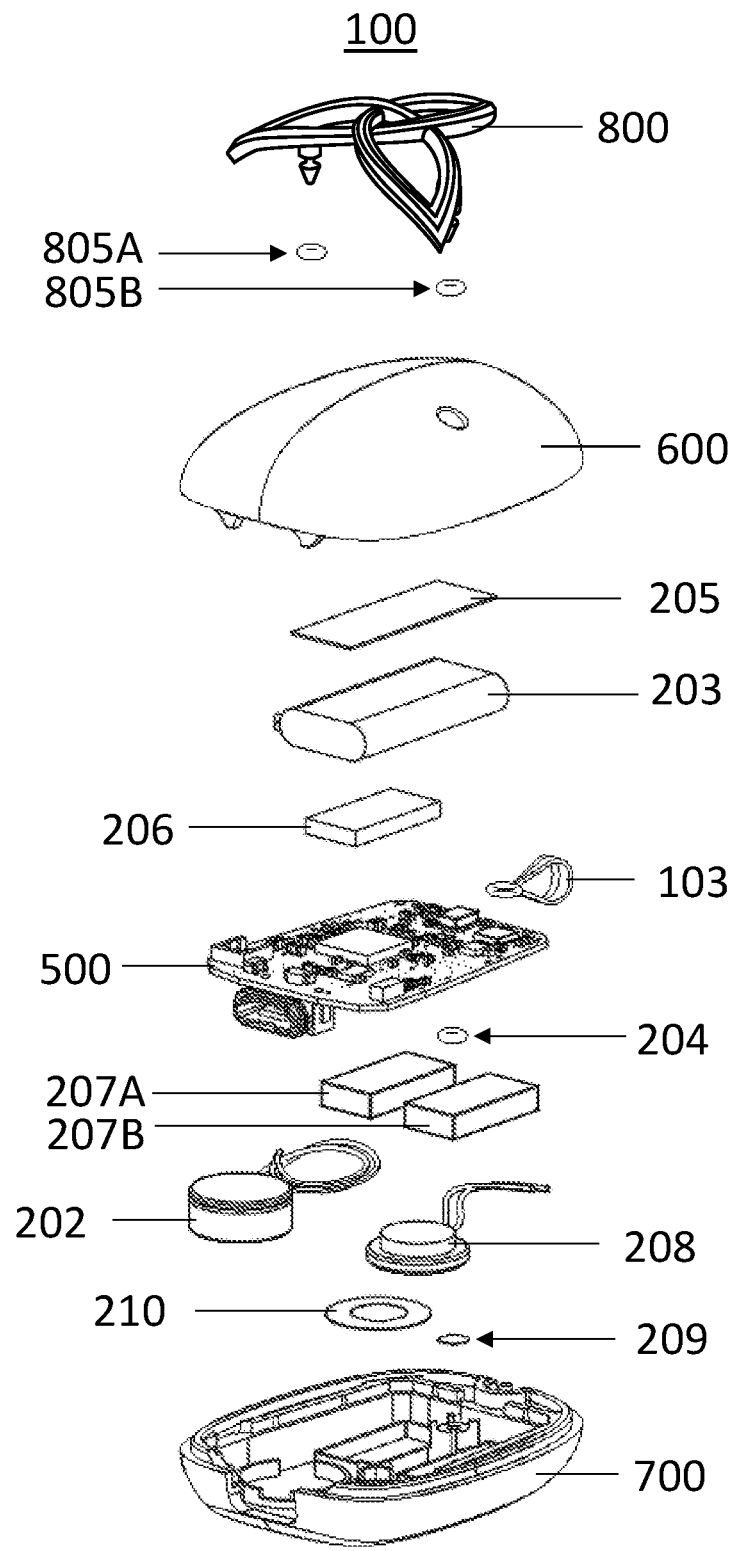
FIG. 2 is an exploded view of the monitor of FIG. 1.

An example of details of the construction of the monitor 100 are shown in FIG. 2. A speaker moisture barrier 210 and a microphone moisture barrier 209 can be adhered to the bottom housing 700. These moisture barriers 210, 209 allow sound to pass through while protecting against water ingress. An audible alert transducer, such as a speaker 208 can provide audible feedback to assist in locating the monitor 100 when it is lost. A vibration transducer such as a vibration motor 202 can provide tactile feedback to the wearer in the form of a vibratory alert when one or more characteristics of his or her voice is detected to meet configurable sound criteria. Both the speaker 208 and the vibration motor 202 can be electrically connected to a printed circuit board (PCB) 500 such as through wires that can be soldered to plated through-holes in the PCB 500. In other embodiments, the speaker 208 and/or vibration motor 202 may be electrically connected to the PCB 500 such as through any of various means such as direct solder connection, wires with crimped connector pins, or wires soldered to surface-mount pads.

An O-ring can be sized and shaped act as an acoustic gasket 204 between the bottom housing 700 and the PCB 500.

A pair of magnets 207A, 207B can be included, such as can be glued inside wells in the bottom housing 700. The magnets 207A, 207B can allow the monitor 100 to be worn as a lapel pin such as by using a ferromagnetic washer that can be placed inside the wearer's clothing, garment, or fashion accessory for example. In other embodiments, suitable magnetic or magnetizable material can be employed instead of or in addition to the magnets 207A, 207B and the washer. Other examples of such fasteners can include at least one of a clip, a pin, a pendant, or a bail.

An insulating pad 206 can be positioned between the PCB 500 and a battery 203, such as to insulate the exterior of the battery 203 from the PCB 500. A piece of double-sided tape 205 can be included, such as to secure the battery 203 to an inside of the top housing 600.

Figure 3:
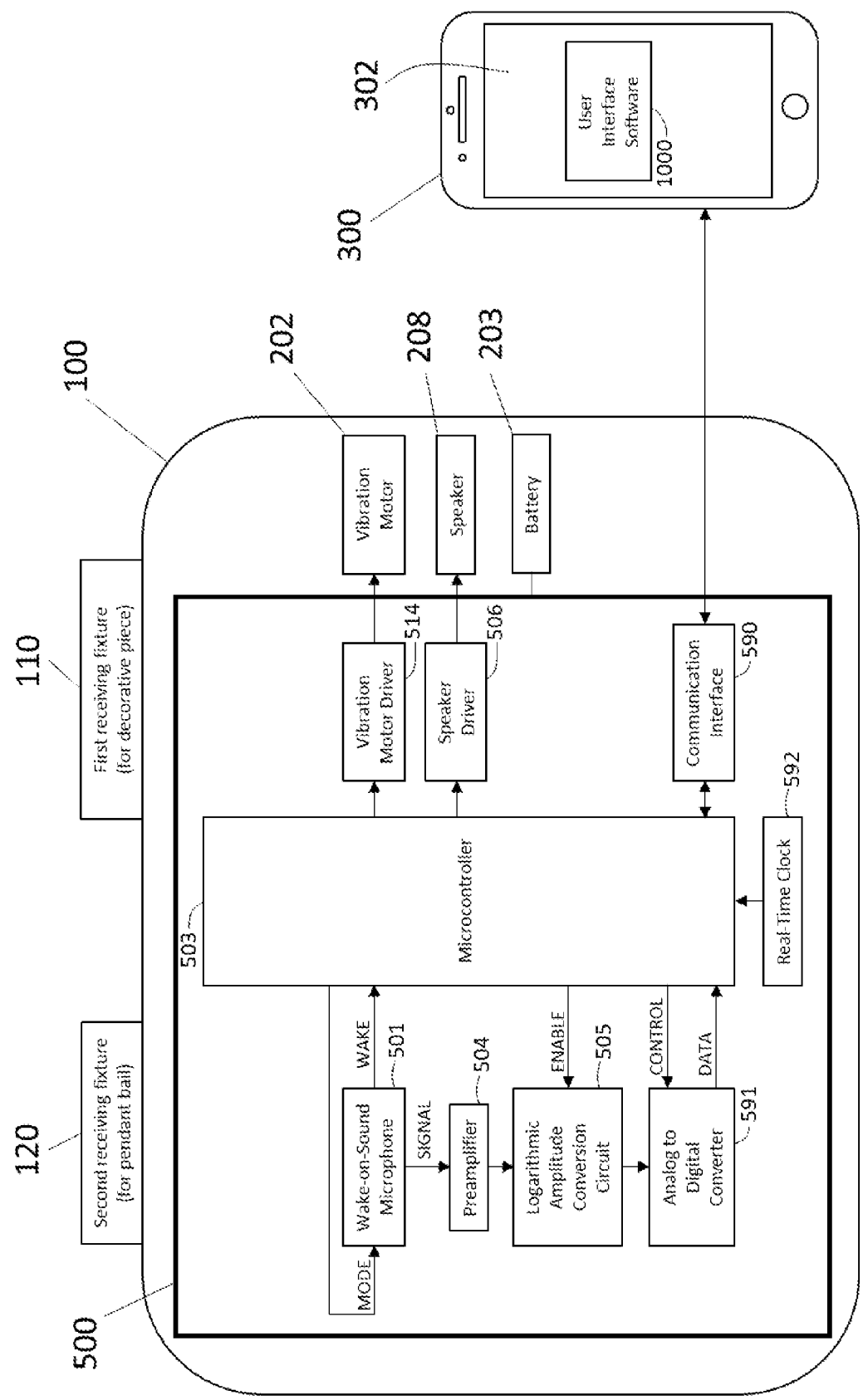
FIG. 3 is a block diagram of components in a first example of the monitor of FIG. 1, also showing an auxiliary smart phone.

FIG. 3 is a block diagram of an example of certain components in the system including the monitor 100. The system can include the wearable monitor 100 and a separate local or remote auxiliary device 300, such as a scheduling device that can include a portable electronic device such as a smart phone auxiliary device 300. The smart phone auxiliary device 300 can include memory storing instructions that can be executable by an onboard controller circuitry to provide user interface software 1000, and can have a touchscreen 302. The user interface software 1000 can include graphical user interface software (GUI). Auxiliary device controller circuitry, coupled to the GUI, can receive input to generate a schedule for the sound criteria that can change, such as based on time-of-day and/or day-of-week. The schedule can be communicated over an auxiliary device communications interface to a communications interface 590 of the monitor 100. In other embodiments, the auxiliary device 300 can include an electronic device such as a personal computer. For example, the personal computer or other electronic device can employ a human interface, such as can include a user input device such as a keyboard, mouse or touchscreen.

The monitor 100 can incorporate a first receiving fixture 110 such as for attaching the decorative piece 800 (see below) and a second receiving fixture 120 for attachment of the pendant bail 103 (see below).

The monitor 100 can include the vibration motor 202, the speaker 208, the battery 203, and the PCB 500. The PCB 500 can include a sound transducer such as a wake-on-sound microphone 501 that can produce an electrical sound signal in response to sound, and onboard controller circuitry that receives the electrical sound signal, performs signal-processing, and generates an alert indication in response to a determination that a voice of the user wearing the device meets one or more sound criteria, which may include any combination of volume level, frequency, nasality or keyword recognition. The onboard controller circuitry can include a preamplifier 504, a logarithmic amplitude conversion circuit 505, an analog to digital converter (ADC) 591, a microcontroller 503 and a real-time clock 592. The PCB 500 can also include a vibration motor driver circuit (hereinafter "vibration motor driver") 514 that can activate the vibration motor 202 such as in response to the alert indication from the onboard controller circuitry. The PCB 500 can further include a speaker driver circuit (hereinafter "speaker driver") 506, and onboard communications interface circuitry that can implement a communications interface 590. In an embodiment, the communication interface 590 is a wireless interface such as Bluetooth® Low Energy. Further or alternatively, the communication interface 590 can include a wired interface such as a USB port. The real-time clock 592 can include a timekeeping circuit that includes logic to report the current time, such as with separate fields for seconds, minutes, hours, and day of week. The real-time clock can also include logic for month, day of month and year, including special logic for leap years.

The microcontroller 503 can provide one or more "CONTROL" signals to the ADC 591, and can receive one or more "DATA" signals from the ADC 591, including at a mode-switch input of the onboard microcontroller circuitry. The microcontroller 503 can receive a "WAKE" signal from the wake-on-sound microphone 501 (e.g., in response to a received sound at a level exceeding a predetermined wakeup threshold during the sleep mode) and provides a "MODE" control signal to the wake-on-sound microphone 501. The microcontroller 503 can provide an "ENABLE" signal to the logarithmic amplitude conversion circuit 505.

Figure 4:
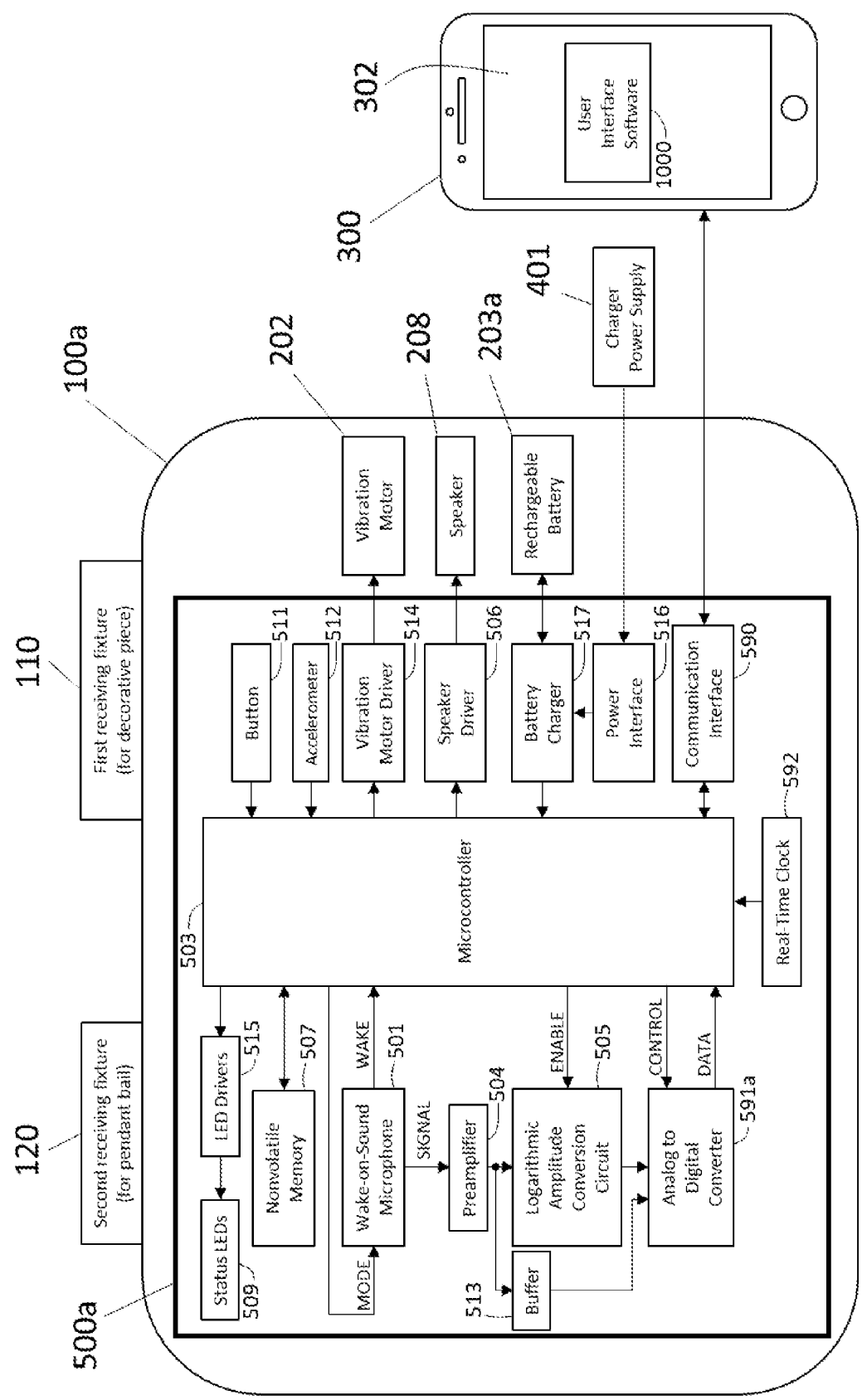
FIG. 4 is a block diagram of components in a second example of the monitor of FIG. 1, also showing a smart phone and a charger power supply.

FIG. 4 is a block diagram of an example of certain components in a monitor 100a. The monitor 100a can include additional components compared to the monitor 100. Additional circuits on a PCB 500a can include status LEDs 509, LED drivers 515, nonvolatile memory 507, a button 511, an accelerometer 512, a battery charging circuit (hereinafter, "battery charger") 517, a battery charging power interface 516, and an audio signal buffer (hereinafter, "buffer") 513. The power interface 516 can for example be a USB charging port. Furthermore, a battery 203a can be a rechargeable battery, and an analog to digital converter (ADC) 591a can include a second input connected to an output of the buffer 513. Measurement of the buffered audio signal can help preserve the frequency content of the sound signal, which is not maintained by the logarithmic amplitude conversion circuit 505. Power can be applied to the rechargeable battery 203a through the power interface 516. A charger power supply 401 is connectable to the power interface 516.

A screenless user interface can be provided. For example, the microcontroller 503 can be configured to respond to presses of the button 511. One button press results in the monitor 100a allowing connection over its communication interface 590. A second button press within a specified window of time, for example ten seconds, enables monitor mode (see below). A long duration button press disables monitor mode and turns off the monitor 100a.

Circuitry located between an output of the microphone 501 and an input of the ADC 591 or 591a falls under the general category of a signal conditioning circuit. In FIG. 3, the signal conditioning circuit can include the preamplifier 504 and the logarithmic amplitude conversion circuit 505. In FIG. 4, a further signal conditioning circuit can include the preamplifier 504 and the buffer 513.

The nonvolatile memory 507 can be included such as to provide data logging capability. For example, the nonvolatile memory 507 can store timestamped records of voice volume levels. Thereby, the wearer or caregiver or other person responsible for the wearer can review the history of the voice volume of the wearer, vibration events and schedule changes (see below). The nonvolatile memory 507 can also be used to record the sounds that produced a vibration alert, such as for later review.

Reinforcement of positive behavior changes is an important aspect of behavior modification, and logging data over time allows improvements to be demonstrated. This is in contrast to ordinary daily use of the monitor 100a, such as in which the monitor 100a only responds to negative sound criteria observations. Data logs can be downloaded from the nonvolatile memory 507 on the monitor 100a to an auxiliary device 300 via the communication interface 590. In the illustration, the auxiliary device 300 is a smart phone 300 implementing a handheld portable user interface. The user interface software 1000 can provide rewards, for example, in the form of achievements. Once the data logs are on the smart phone 300, they can be uploaded to a user account stored on a remote network, and data can be shared with authorized parties.

For example, the data logs can enable sharing progress with parents and support groups. Data logs can also be used by the user interface software 1000 to determine a threshold setting that would produce a desired number of vibratory alerts. This feature can be used to achieve a gradual reduction in voice volume that is not overly discouraging to the wearer. For example, the user interface software 1000 can be configured to report a threshold that would have produced a maximum of five vibrations per hour, and such threshold can be incorporated into a threshold schedule (see below) for the next day.

The status LEDs 509 can be combined within a single package, although this is not essential. Light holes and/or light piping may optionally be provided. In an example, there are no light holes or light piping. This is because the enclosure 900 is configured such that light penetration through walls of the enclosure 900 is sufficient. A combination of variable light colors, together with solid or blinking illumination patterns, can be used to indicate certain aspects of functioning of the monitor 100a. For example, such aspects can include battery charging progress, wireless connection status, and live monitor mode status (see below). LED 509 usage can be reserved for temporary conditions or when external power is present, such as to help maximize battery life.

The accelerometer 512 can be configured to sense vibrations, such as can be used to detect sounds via accelerometer-sensed vibrations; the vibrations being coupled from the air, into the enclosure 900, and finally into the PCB 500a on which the accelerometer 512 is mounted. The accelerometer 512 can also be used to detect user input (e.g., via tapping) or to detect activity and motion of the wearer and orientation of the monitor 100a. Combining data from multiple sensors to create a new reading or to make a decision can be referred to as sensor fusion. Sensor fusion of any two or all three of the following parameters can be utilized to obtain more accurate sound detection: a digitized logarithmic amplitude conversion signal, readings of the accelerometer 512, and a buffered audio signal (see below). That is, software of the monitor 100a can provide sensor fusion of data derived from the wake-on-sound microphone 501 and data derived from the accelerometer 512. The accelerometer 512 may also be used in place of button activation, for example, wherein bumps or manipulations or tapping of the monitor 100a can be detected via the accelerometer 512, such as can provide information similar to that described herein with respect to button presses.

Control of the monitor 100a may also be achieved by voice control through the application of speech recognition algorithms to the buffered audio signal (see below). Recognition of one or more predefined voice-command key words can be achieved on the microcontroller 503 such as by training a neural network and loading a model of the neural network into the microcontroller 503. Alternately, customized key words can be recorded by the user and a comparison algorithm applied to determine when the buffered audio signal matches the customized key word above a certain confidence level. The monitor 100a can also be configured to issue one or more vibration alerts when a certain word or words are detected.

Figure 5A:
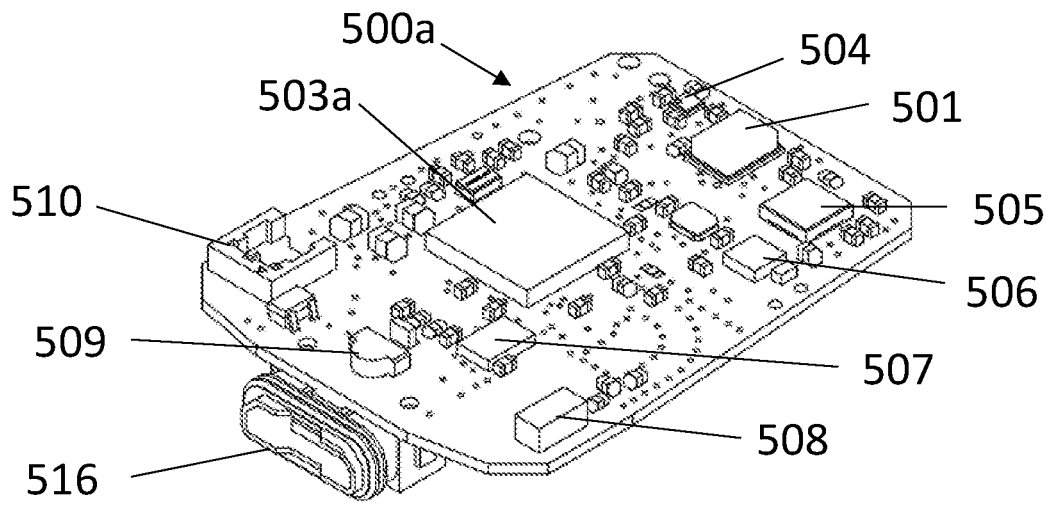
FIG. 5A is a top perspective view of a printed circuit board of the second example of the monitor.
Figure 5B:
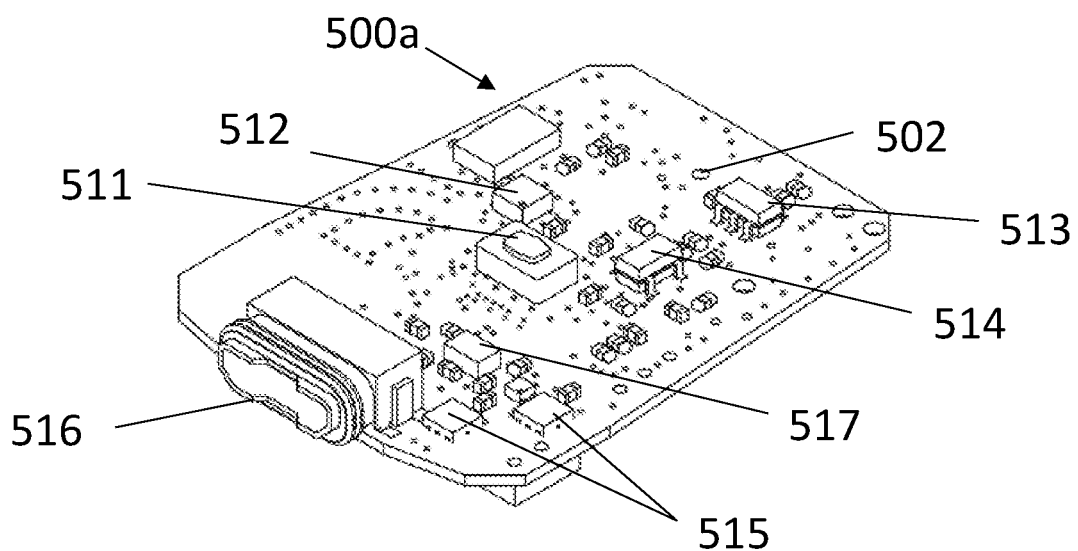
FIG. 5B is a bottom perspective view of the printed circuit board of the second example of the monitor.

FIG. 5A and FIG. 5B provide detailed views of an example of the top side and bottom side of the PCB 500a, respectively. The wake-on-sound microphone 501 can be mounted on the top side, and its microphone port can face the bottom side such as through a hole in the PCB 500a. The microcontroller 503 can be mounted on the top side of the PCB 500a. In FIG. 5A, a microcontroller 503a is shown. The microcontroller 503a can incorporate the microcontroller 503, the analog to digital converter 591, the real-time clock 592, and a part of the communication interface 590. An antenna 508 can also be included in or coupled to the communication interface 590. The preamplifier 504, the logarithmic amplitude conversion circuit 505, the speaker driver 506, the nonvolatile memory 507, the status LEDs 509 and a battery connector 510 can also be positioned on the top side of the PCB 500a.

The bottom side of the PCB 500a includes the button 511, the accelerometer 512, the vibration motor driver 514, the LED drivers 515, the power interface 516 and the battery charger 517. The audio signal buffer 513 is also included to allow the audio signal to be input to a separate analog to digital converter channel. This audio signal can be recorded to keep a history of sound events, or it can be analyzed for frequency content to enhance the selectivity of the monitor 100a to the wearer's voice.

Figure 6A:
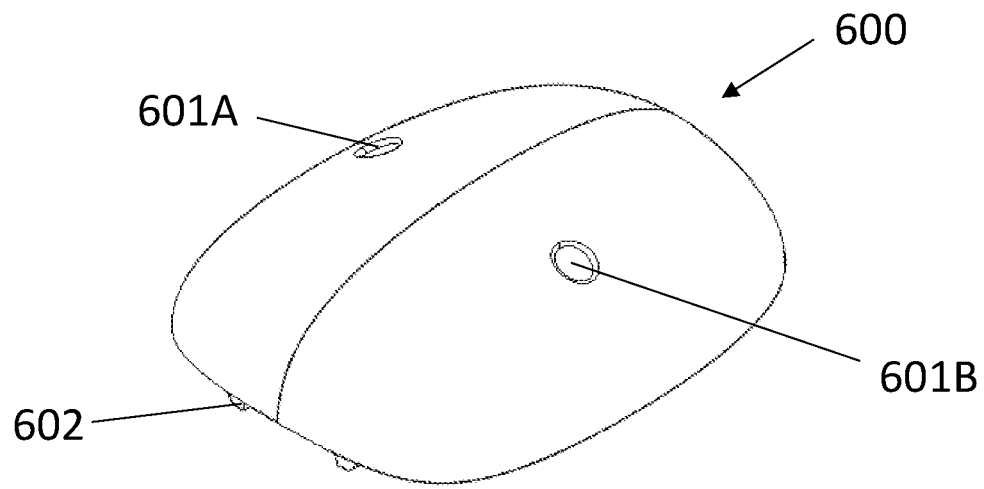
FIG. 6A is a perspective view of an outside of a top housing of the monitor of FIG. 1.
Figure 6B:
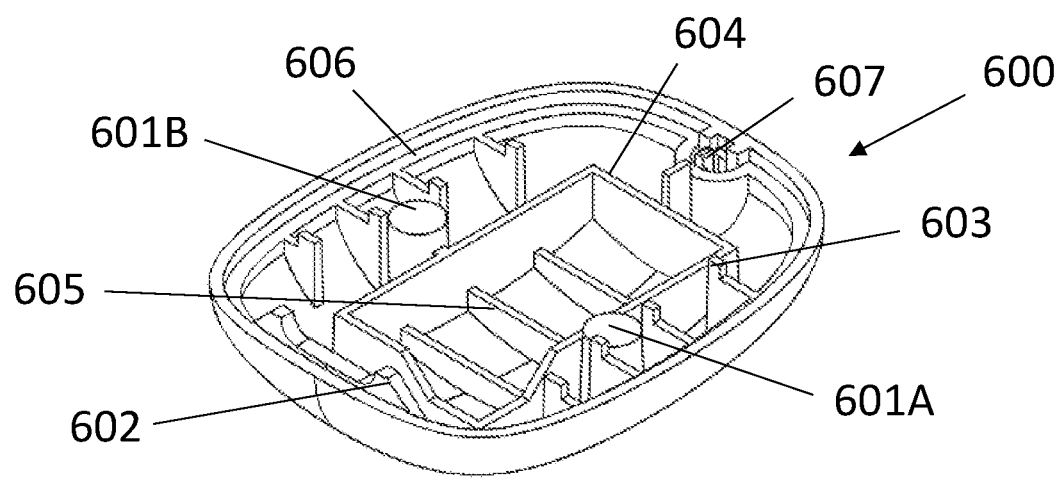
FIG. 6B is a perspective view of an inside of the top housing of the monitor of FIG. 1.

FIG. 6A and FIG. 6B provide detailed views of the outside and inside of the top housing 600, respectively. The top housing 600 can be made of flexible plastic, for example. The holes 601A, 601B in the top housing 600 form the first receiving fixture to receive the user-attachable and user-detachable decorative piece. The holes 601A, 601B are sealed at the bottom, that is, they are blind holes. The holes 601A, 601B can provide channels to engagingly receive corresponding prongs 801A, 801B of the decorative piece 800 (see below). A watertight seal can be provided at the power interface 516 of the PCB 500a such as by inclusion of a connector bulkhead 602. The inside of the top housing 600 can include PCB hold-down protrusions 603. The battery 203 or 203a can be held in place by walls of a battery well 604, and by battery support ribs 605. The top housing 600 also includes a bail post socket 607, and a flat adhesive mating surface 606.

Figure 7A:
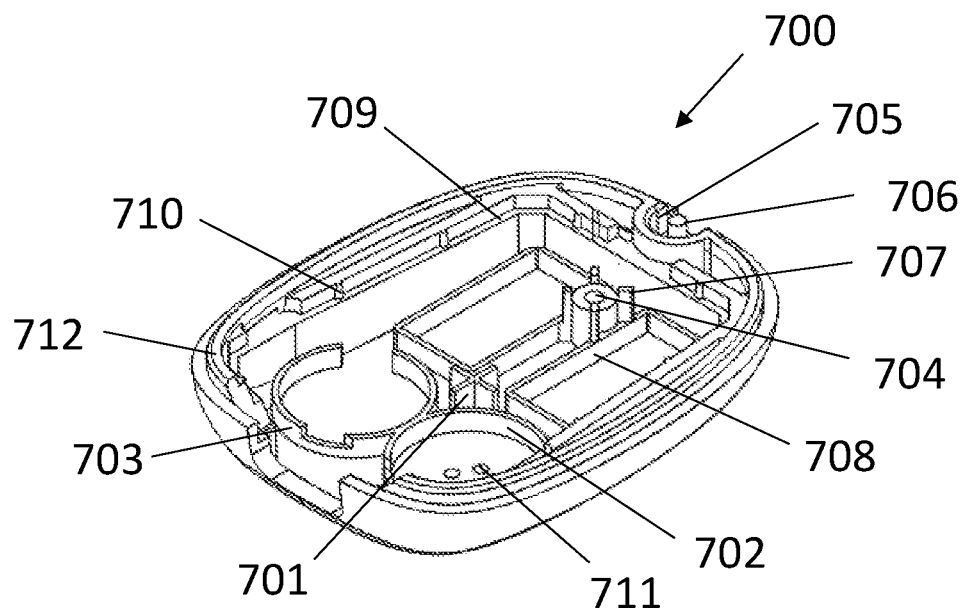
FIG. 7A is a perspective view of an inside of a bottom housing of the monitor of FIG. 1.
Figure 7B:
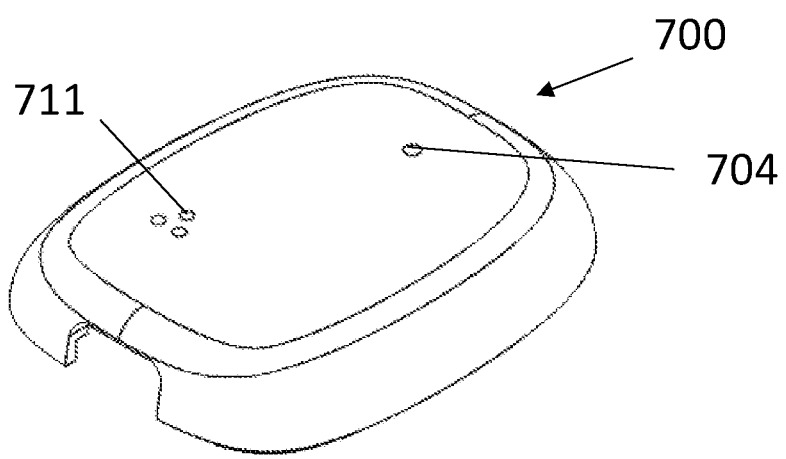
FIG. 7B is a perspective view of an outside of the bottom housing of the monitor of FIG. 1.
Figure 8A:
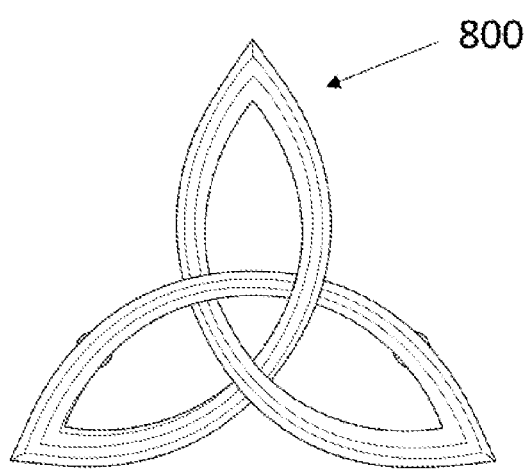
FIG. 8A is a top plan view of the decorative piece of FIG. 1.
Figure 8C:
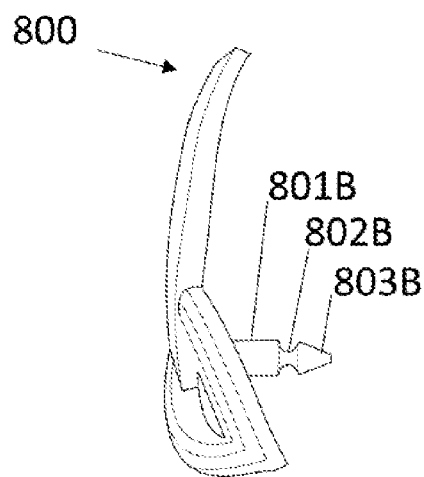
FIG. 8C is a right side elevation view of the decorative piece of FIG. 1.
Figure 8B:
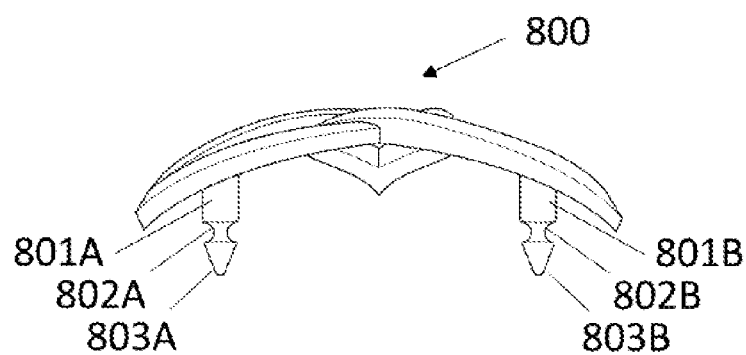
FIG. 8B is a front elevation view of the decorative piece of FIG. 1.
Figure 8D:
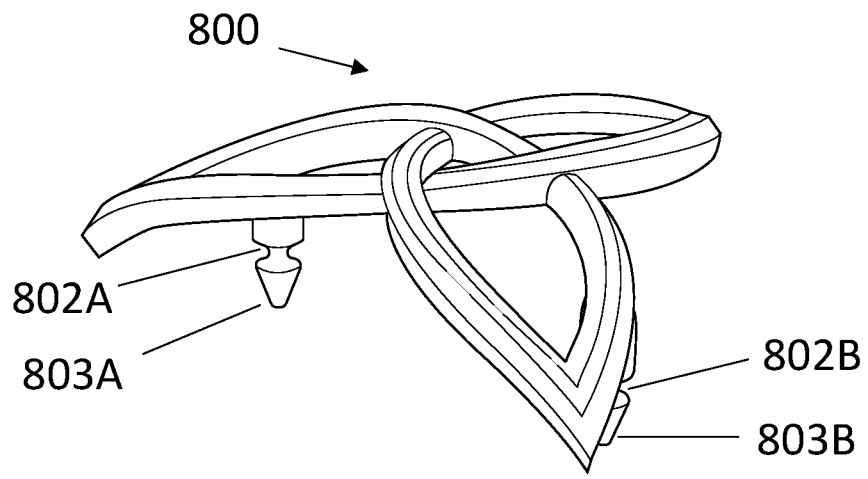
FIG. 8D is an upper perspective view of the decorative piece of FIG. 1.
Figure 8E:
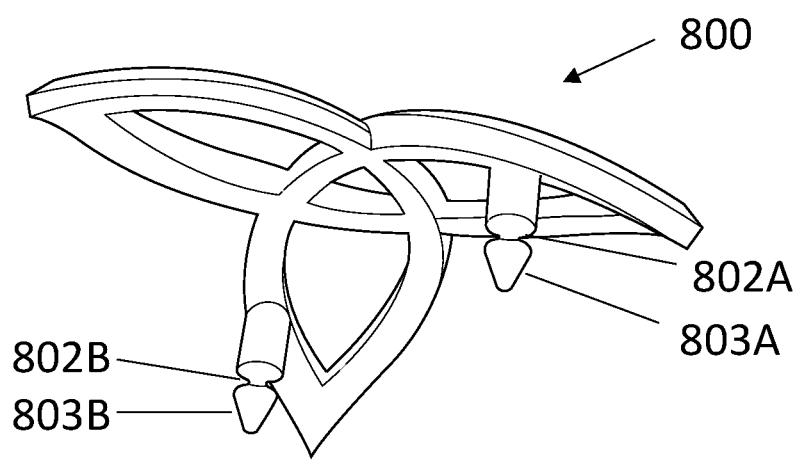
FIG. 8E is a lower perspective view of the decorative piece of FIG. 1.

FIG. 7A and FIG. 7B provide detailed views of an example of the inside and outside of the bottom housing 700, respectively. The bottom housing 700 can be made of flexible plastic, for example. A button interface column 701, which can be shaped like a '+' (plus) sign, makes contact with the button 511 on the bottom side of the PCB 500a. When the bottom housing 700 is squeezed, it flexes and the button interface column 701 presses the button 511. The speaker 208 can be held in place by a wall of a speaker well 702, while the vibration motor 202 can be held in place by a wall of a vibration motor well 703. An acoustic port 704 can be formed by a hollow column that places the acoustic gasket 204 in contact with the bottom of the PCB 500 or 500a. The acoustic gasket 204 can be held in place during assembly by retention posts 707. The bottom housing 700 can also include a bail channel 705 and bail post 706. During assembly of the monitor 100a, the bail 103 can be placed into the bail channel 705 surrounding the bail post 706, and the bail post 706 can be engagingly received in the bail post socket 607 of the top housing 600. The bail channel 705, bail post 706 and bail post socket 607 can collectively serve as the second receiving fixture 120 such as depicted in FIG. 3 and FIG. 4. The magnets 207A, 207B can be held in place by walls of magnet wells 708.

The top housing 600 and bottom housing 700 can be made to look like one or more natural objects such as one or more of rocks, minerals or wood or given another decorative pattern such as by printing the desired pattern on a film and such as by using a water-transfer process such as hydrodipped-printing ("hydrodipping") to apply the graphics texture to the surface of the housing.

Figure 23A:
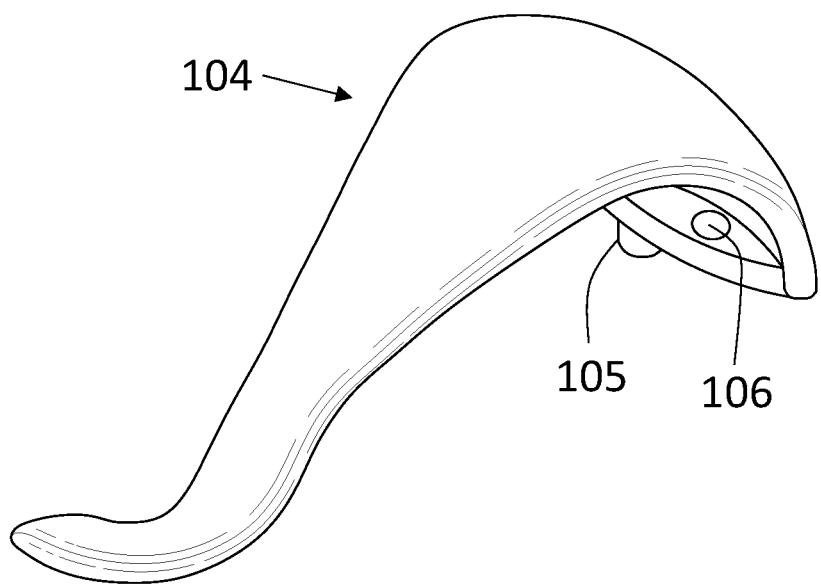
FIG. 23A is a top perspective view of bail half designed to allow user attaching and detaching.
Figure 23B:
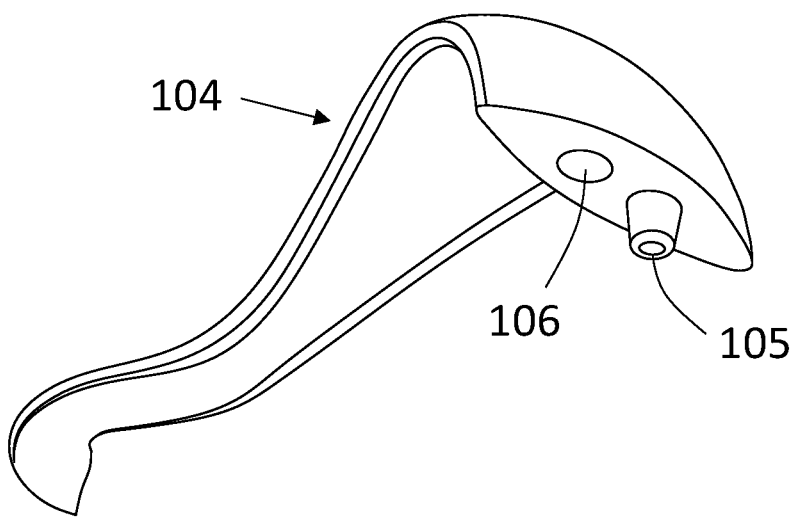
FIG. 23B is a bottom perspective view of a bail half designed to allow user attaching and detaching.
Figure 23C:
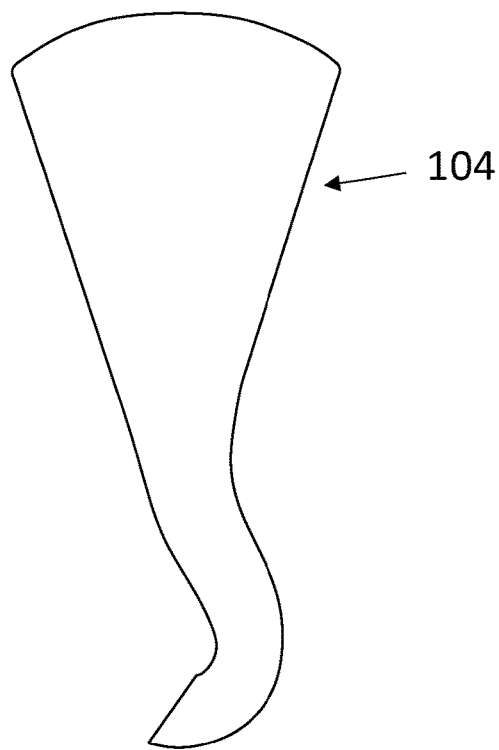
FIG. 23C is a top plan view of a bail half designed to allow user attaching and detaching.
Figure 23D:
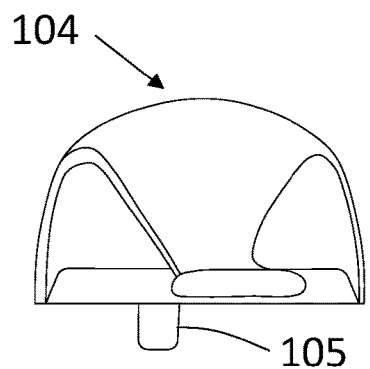
FIG. 23D is a front elevation view of a bail half designed to allow user attaching and detaching.
Figure 23E:
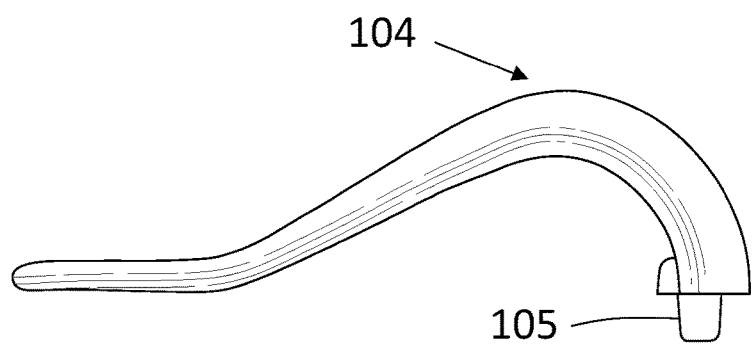
FIG. 23E is a right side elevation view of a bail half designed to allow user attaching and detaching.

In order to allow users to change between bail attachment and magnetic attachment, a user-attachable and user-detachable pendant bail 103a can be constructed from two bail halves 104 such as shown in FIG. 23A (top perspective view), FIG. 23B (bottom perspective view), FIG. 23C (top plan view), FIG. 23D (front elevation view) and FIG. 23E (right side elevation view). The bail halves 104 can be identical, although this is not required, such as by being configured with rotational symmetry and incorporating a cylindrical protrusion 105 and a hole 106 that can mate together such as when the two bail halves 104 are placed back to back.

Figure 25A:
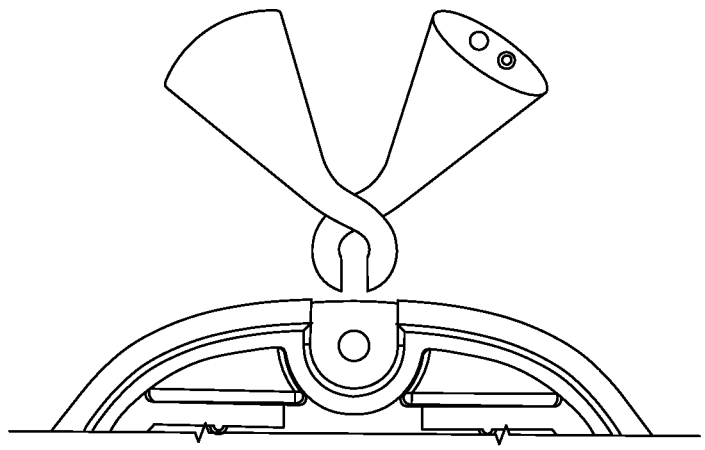
FIGS. 25A-25C are top plan views of two bail halves and the bail post at various stages of the attachment process.
Figure 25B:
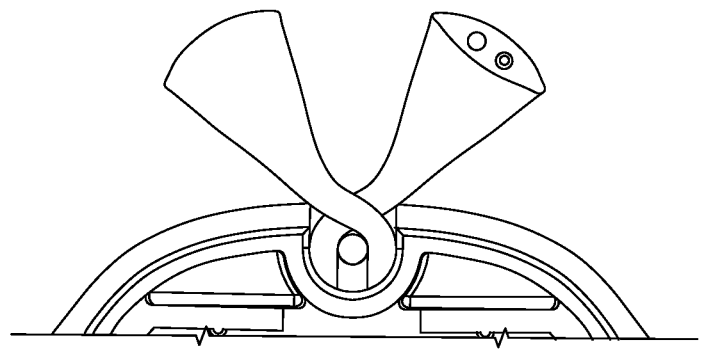
Figure 25C:
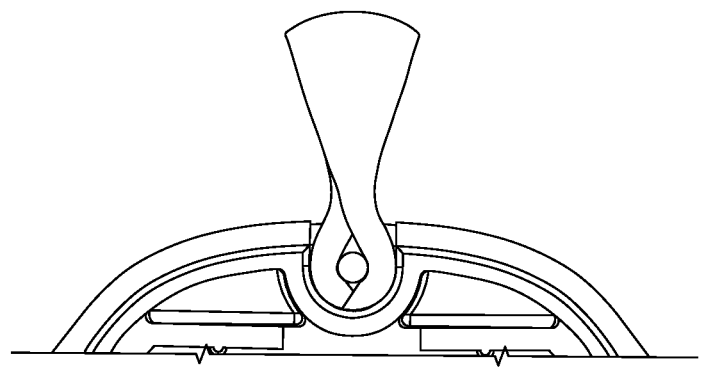

The narrow-end of the bail halves 104 can be curved and angled such that it clears the bail post 706 when rotated such as shown in FIG. 24A and FIG. 25A before insertion and FIG. 24B and FIG. 25B after insertion. Note that in FIGS. 24A-24E and FIGS. 25A-25C, the top housing 600 (not shown) has been omitted for clarity. Following insertion, the bail halves 104 can be rotated towards each other in one direction, while pulling them apart in the other direction to avoid interference with the cylindrical protrusions 105 such as shown in FIG. 24C. Since the bail halves 104 are constrained between the bottom housing 700 and top housing 600, this pulling apart can help build up a spring force in the bail halves 104. Once the cylindrical protrusions 105 are aligned with the holes 106, such as seen in FIG. 24D, the bail halves 104 can be released, and the spring force pushes them together as shown in FIG. 24E and FIG. 25C.

In addition to allowing users to attach and detach the bail depending on whether they want to wear the device as a necklace or a magnetically held lapel pin, having a pendant bail 103a that can be installed around the bail post 706 after the bottom housing 700 and top housing 600 have been secured together to form enclosure 900 allows the plating on the bail 103a to match the plating on the decorative piece 800, such as both being selected and installed immediately prior to product shipping according to customer demand. Furthermore, customers may choose multiple decorative pieces 800 with different plating options and change out the bail 103a to match each different decorative piece.

Returning to FIG. 7A and FIG. 7B, a ledge can be provided in the bottom housing 700, thereby defining a support surface 709 for the PCB 500 or 500a. Crush ribs 710 can be included along the ledge such as to help retain the PCB 500 or 500a. Speaker holes 711 in the speaker well 702 can allow sound to escape the bottom housing 700. A raised adhesive mating surface 712 can extend around the perimeter of the bottom housing 700, and can provide a tight seal when the bottom housing 700 is mated with the top housing 600.

The decorative piece 800 is depicted from several angles in the examples of FIGS. 8A-8E. The back surface of the decorative piece 800 can conform to the top surface curvature of the top housing 600. The prongs 801A, 801B can extend from the back of the decorative piece 800, and can fit without interference into the holes 601A, 601B in the top housing 600. The diameter of the lower portion of each of the prongs 801A, 801B can be reduced such as to provide grooves 802A, 802B for receiving retention O-rings 805A, 805B (see FIG. 2). The retention O-rings 805A, 805B can provide an interference fit with the inside walls of the holes 601A, 601B. The retention O-ring 805A, 805B material can be compliant, such as for allowing the retention O-rings 805A, 805B to be inserted into the holes 601A, 601B and deform. The deformed retention O-rings 805A, 805B can help provide adequate interference holding force while they remain in the holes 601A, 601B. Nevertheless, the compliant interference fit can still allow the decorative piece 800 to be conveniently removed when needed. Bottom ends 803A, 803B of the prongs 801A, 801B can be pointed such as to ease assembly of the retention O-rings 805A, 805B onto the prongs 801A, 801B.

Figure 9:
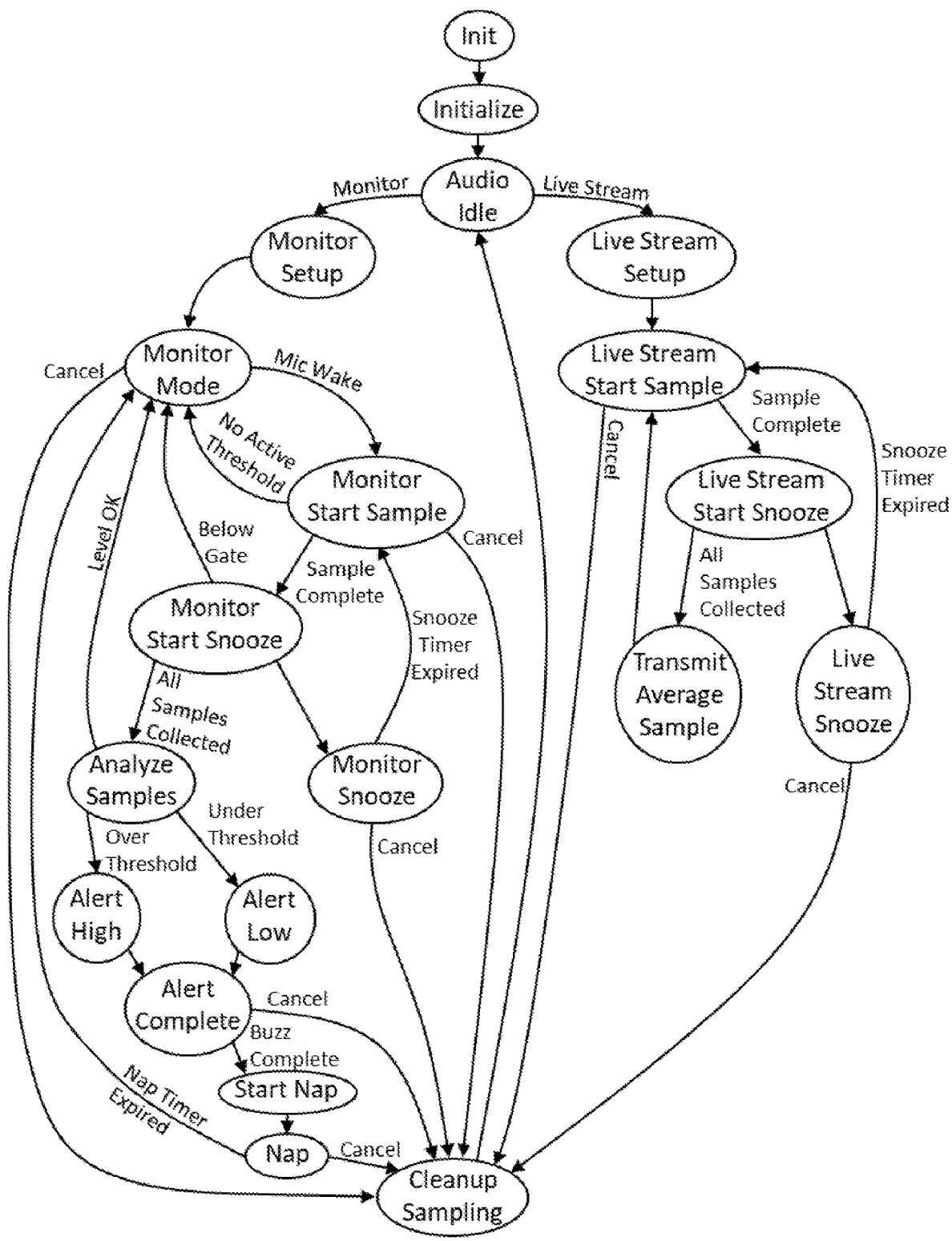
FIG. 9 is an example of a flowchart of portions of a method of operating a wearable voice volume monitor, showing operation in a monitor mode and in a live stream mode.
Figure 10:
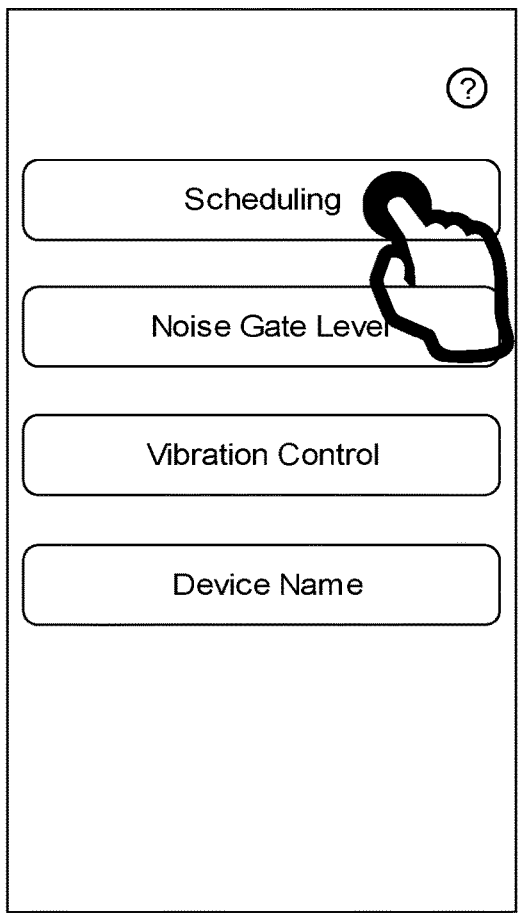
FIGS. 10-21 depict wireframes of screens displayed on a smart phone when the smart phone is used to set a monitoring schedule for an exemplary wearable voice volume monitor.
Figure 11:
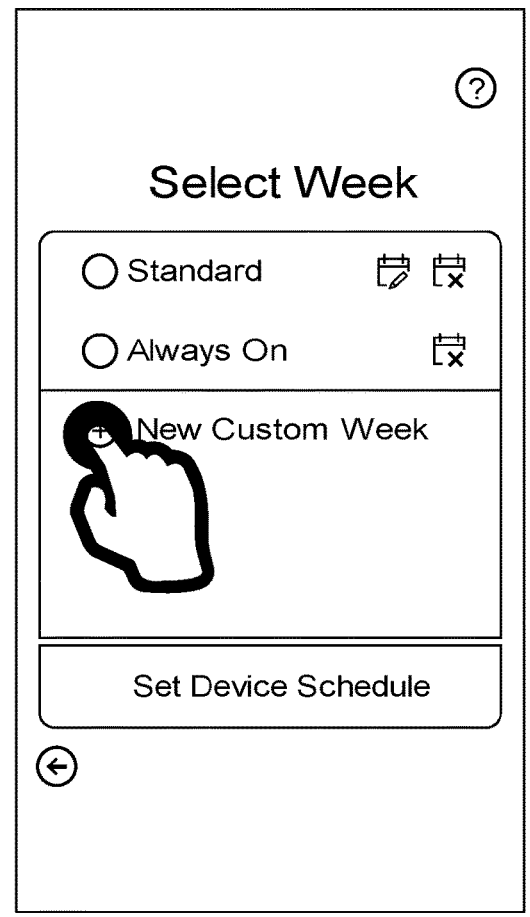
Figure 12:
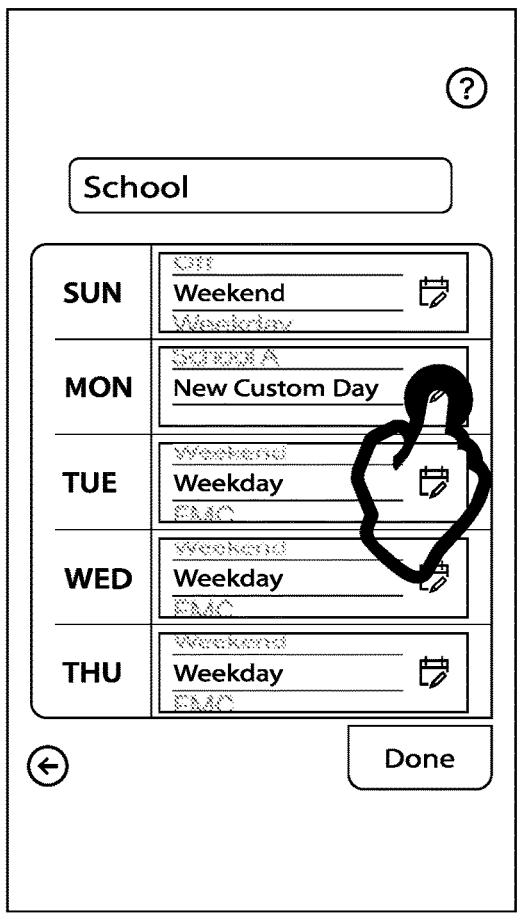
Figure 13:
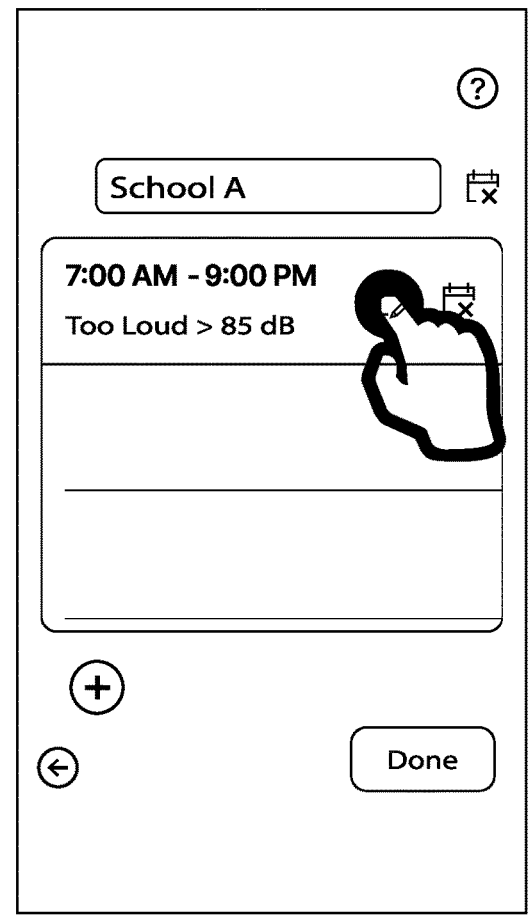
Figure 14:
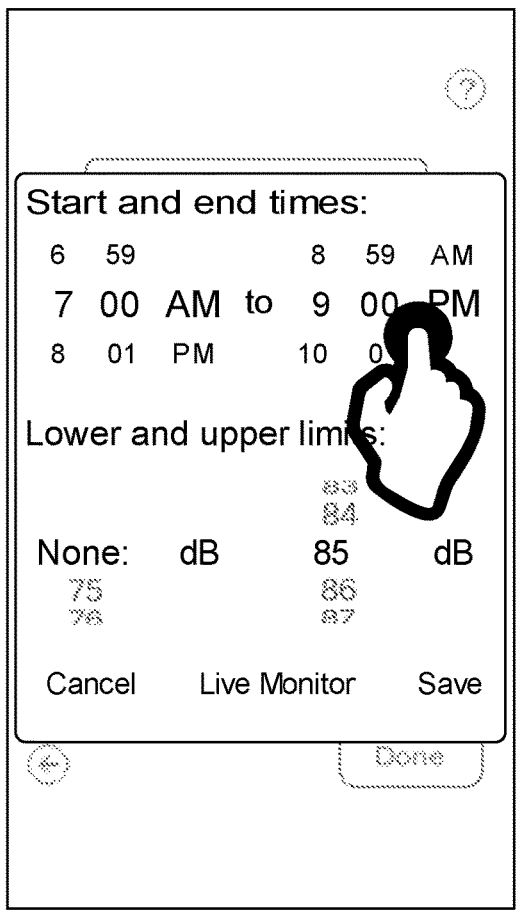
Figure 15:
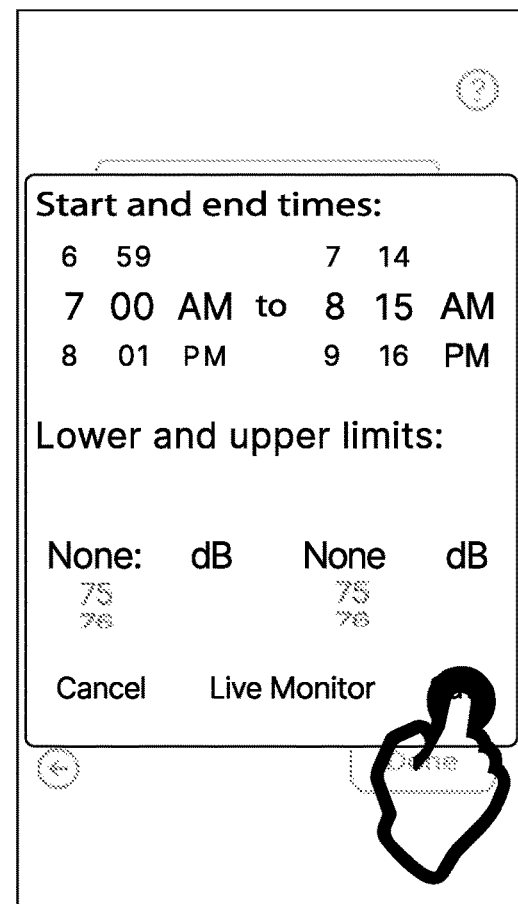
Figure 16:
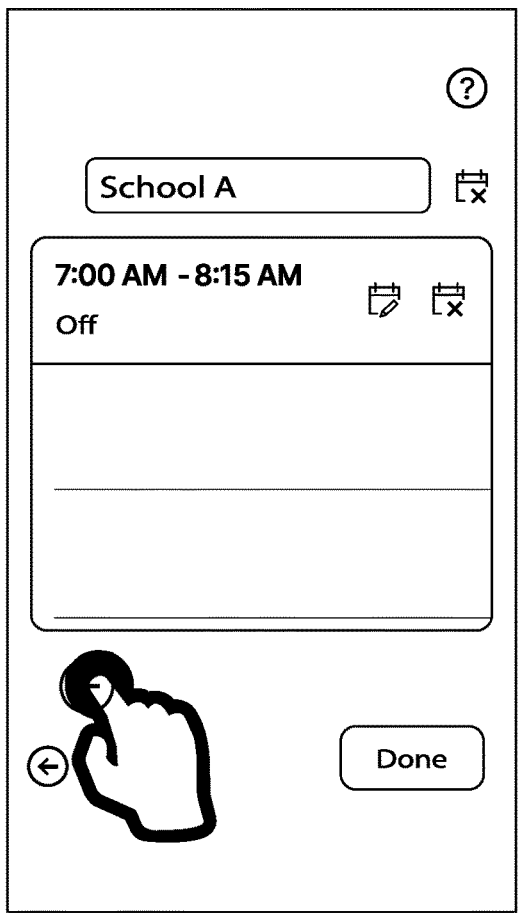
Figure 17:
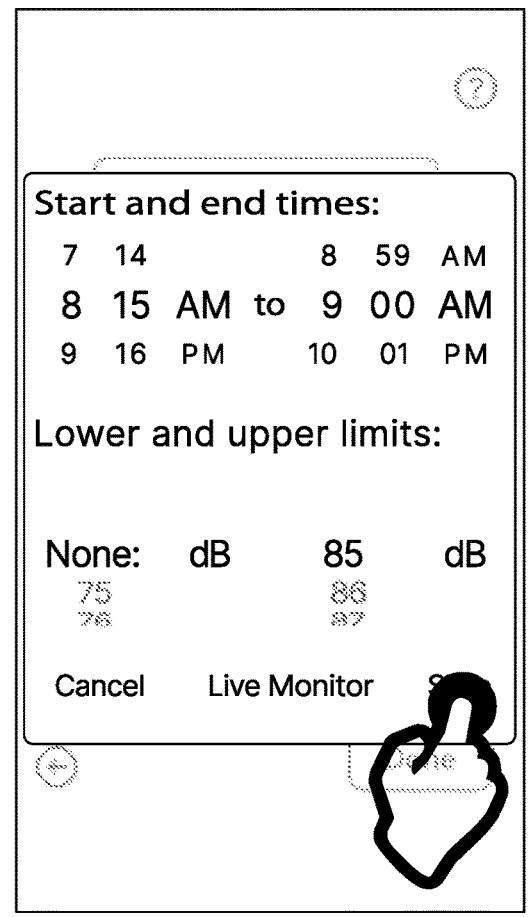
Figure 18:
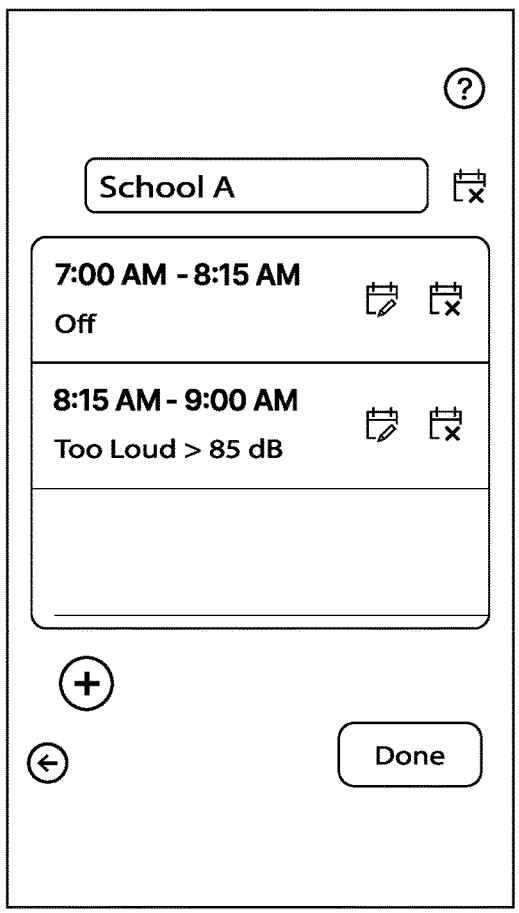
Figure 19:
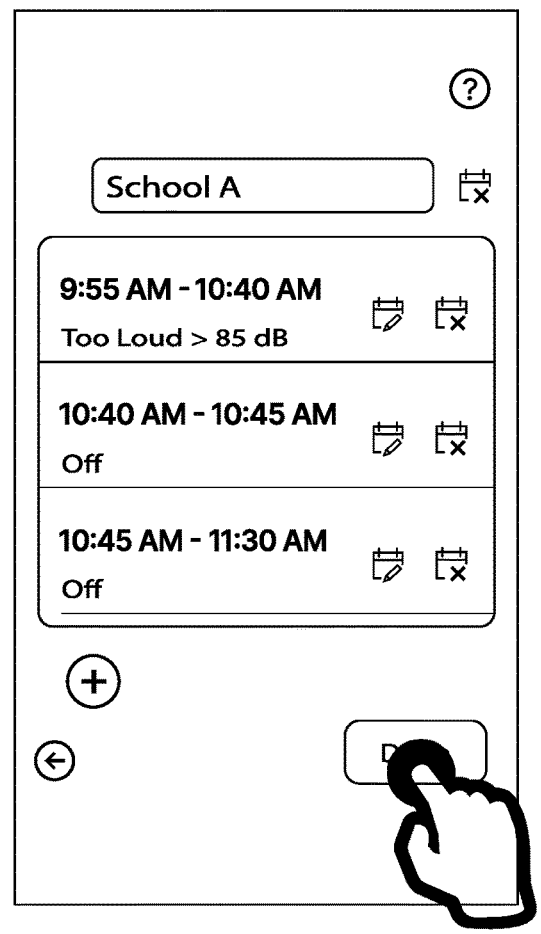
Figure 20:
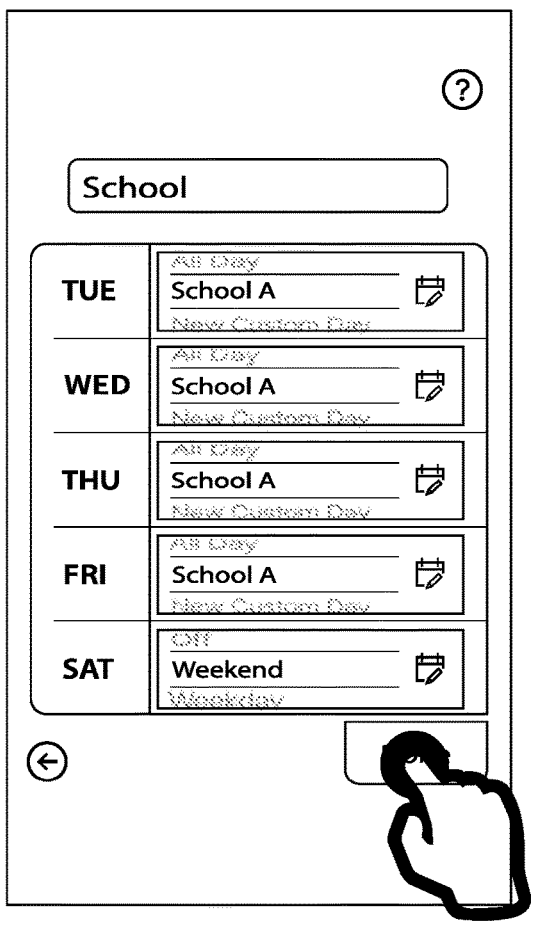
Figure 21:
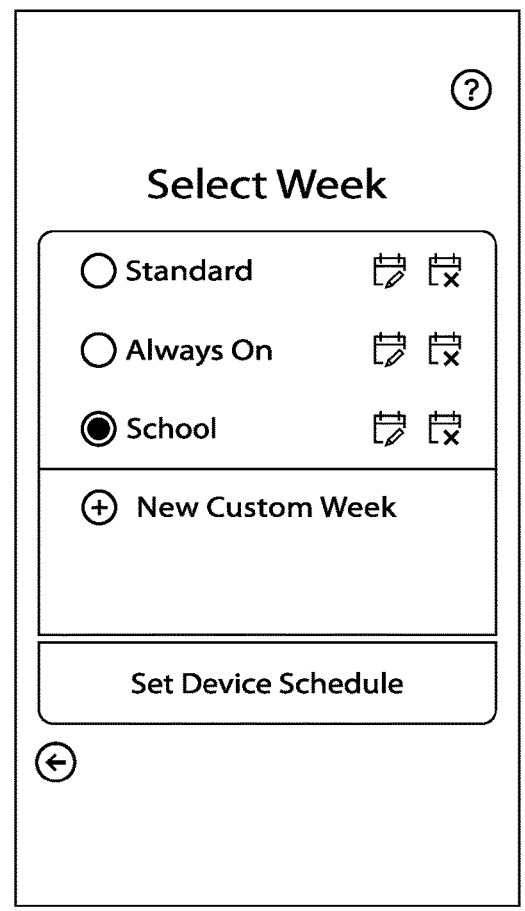

FIG. 9 is a flowchart of an example of operation of a wearable voice monitor, showing operation of the monitor 100 or 100a in a "monitor" mode and in a "live stream" mode. The operation can be controlled by the microcontroller 503 or 503a, whether in the monitor 100 or 100a or another embodiment. Software running in the microcontroller 503 can implement a state machine, which can perform certain required functions of the monitor 100 or 100a. In the following description, unless the context indicates otherwise, it can be assumed for convenience that the operation is performed by the microcontroller 503 in the monitor 100a.

Monitor mode involves measuring the voice volume and activating the alert vibration motor 202 if criteria for vibration alert are met. Live stream mode involves continually measuring the voice volume and transmitting the volume level over the communication interface 590 to the auxiliary device 300, such as the smart phone 300. Live stream mode can be useful when first configuring the monitor 100a, such as to determine what thresholds should be set for voice levels. Variations in sound levels can occur, such as can be based on variations in component properties and positioning of the monitor 100a on the wearer, so each wearer may require different thresholds.

In monitor mode, power consumption can be minimized by having the microcontroller 503 remain in a low-power sleep mode until the wake-on-sound microphone 501 detects a sound event. A high level on a WAKE signal from the wake-on-sound microphone 501 can cause the microcontroller 503 to wake up and transition the state machine from "Monitor Mode" to "Monitor Start Sample." Sampling can involve changing a MODE signal to transition the wake-on-sound microphone 501 into a normal mode, asserting an ENABLE signal to activate the logarithmic amplitude conversion circuit 505 to operate in a normal mode, activating the analog to digital converter 591, waiting a brief time for the circuits to be ready for use, and finally sampling the input to the analog to digital converter 591. Once the sample is complete, the state machine can transition to the "Monitor Start Snooze" state. If the first sample collected is below a noise floor or noise gate level, the state machine can be returned to "Monitor Mode" without collecting additional samples. This noise gate feature can be included to help extend battery life such as in the presence of low-level sounds that are loud enough to trigger the wake-on-sound microphone 501 but not loud enough to trigger a vibration alert. Wind noise and background room noise are two potential sources of low-level sound that can be addressed by the noise gate. The noise gate can also allow the monitor to produce vibration alerts for sounds that are above the noise gate level but below a minimum threshold level. This feature can be used to remind a quiet speaking wearer to speak louder.

Several samples can be collected before analyzing the samples. If additional samples still need to be collected, the state machine can enter "Monitor Snooze," such as to help reduce power in between samples. The "Monitor Snooze" power is lower than the active power, but higher than the sleep state power prior to the wake event, because it leaves certain circuits active to be able to quickly take the next sample when the snooze timer has expired. In an implementation, 10 samples are taken at 10 millisecond intervals before analyzing the samples.

To extend operation time per battery charge, the microcontroller 503, wake-on-sound microphone 501 and logarithmic amplitude conversion circuit 509 can be returned to a sleep state in between a series of samples triggered by the wake-on-sound event.

In an embodiment involving the monitor 100, the ADC 591 may digitize only the output of the logarithmic amplitude conversion circuit 505, such that only amplitude information is available for analysis. In another embodiment involving the monitor 100a, the ADC 591a may digitize both the output of the logarithmic amplitude conversion circuit 505 and the output of the audio signal buffer 513 such as to provide both amplitude and frequency information for analysis.

Once the full number of samples have been collected, the state machine can move to an "Analyze Samples" state. The sample analysis includes applying a digital filtering algorithm such as to help make the monitor 100a less susceptible to false triggers. For example, noise filtering and sound impulse rejection can be performed. In embodiments in which the frequency content can be preserved by sampling the output of the audio signal buffer 513, frequencies outside the vocal range can be rejected. One or more additional characteristics of the sound, such as duration and persistence, can be analyzed such as to help improve the selectivity of the monitor 100a to respond to undesired voice volumes while ignoring non-vocal sources of noise. For example, the monitor 100a can be configured such that only sounds that remain above the threshold longer than a specified duration produce a vibration alert. Alternately, the monitor 100a can be configured to only produce vibration alerts if a persistence criterion is met; that is, if a specified number of samples above the threshold are detected within a specified window of time. The availability of frequency content also allows the monitor 100a to provide feedback related to voice pitch and tone, with one possible application being helping deaf speakers reduce the nasality of their speech.

After analysis, the volume level can be compared to one or more currently active thresholds. If the level is OK, the monitor 100a can return to the low-current sleep state of "Monitor Mode." If the level is outside one of the thresholds, and vibrations are enabled on the monitor 100a, the vibration motor 202 can be activated. The monitor 100a can be configurable to issue one or more vibration alerts if the sound level is too high ("Alert High") or if the sound level is too low ("Alert Low"). This flexibility allows the monitor 100a to be used to help people speak quieter or to speak louder. The use of separate vibration states allows different types of vibration to be used for the different alerts. Furthermore, escalating alerts can be provided. Escalating alerts involve providing subtle vibration alerts for sounds that are only slightly over the threshold or last a short period of time; and providing stronger vibration alerts for sounds that are significantly over the threshold, persist for a long duration, or occur above a specified rate. Stronger vibrations can be achieved by increasing the vibration amplitude and/or duration, or applying a rhythmic or pseudo-random or random vibration pattern intended to make the vibrations more noticeable to the wearer.

Once a vibration alert is complete ("Alert Complete"), the state machine can proceed to a "Start Nap" state to prepare for a "Nap" state. In the "Nap" state, the monitor 100a can be placed in a low-current sleep state with the wake-on-sound input disabled. The "Nap" state can continue until the nap timer expires. The purpose of the "Nap" state is to keep the vibration motor 202 from continuously vibrating in the presence of consistently loud noise, thereby helping reduce energy consumption of the vibration motor 202. Since vibration alerts are disabled during the nap time, there is no need to respond to wake-on-sound events during the nap time.

The live stream function can operate on a separate branch of the state machine. Activating live stream moves the state machine into "Live Stream Setup," such as in which the wake-on-sound microphone 501 can be placed into the normal mode and the logarithmic amplitude conversion circuit 505 can be enabled. Once live stream setup is complete, the state machine can progress to "Live Stream Start Sample." Upon completion of a sample, the "Live Stream Start Snooze" state can prepare the monitor 100a to save power in between samples. In between samples, the "Live Stream Snooze" state can be maintained until the snooze timer expires. After all samples have been collected, the state machine can move to a "Transmit Average Sample" state. In this state, the average of the sound level samples can be transmitted to the smart phone 300 over the communications interface 590.

Audio sampling can be canceled from many of the states. When audio sampling is canceled, the "Cleanup Sampling" state can be used to return the state machine to the "Audio Idle" state, in which no activity occurs. Transition from the "Audio Idle" state to the "Monitor Setup" state can occur following a button press. Transition from the "Audio Idle" state to the "Live Stream Setup" state can occur based on a request from the smart phone 300. The "Init" state and "Initialize" state can include one or more tasks specific to the chosen microcontroller 503.

FIGS. 10-21 depict examples of wireframes of screens that can be displayed on the smart phone 300 such as when the smart phone 300 is used for programming or setting a monitoring schedule for an example of a wearable voice volume monitor such as the monitor 100 or 100a. In the following description, unless the context indicates otherwise, it can be assumed for convenience that the procedures are performed for the monitor 100a. In particular, user interface software 1000 of the smart phone 300 can be used to set a custom threshold schedule. For example, voice volume thresholds can be scheduled to change as many times as desired throughout a particular week to accommodate anticipated changes in the wearer's location, situation or circumstances, with such changes anticipated to correlate to corresponding changes to socially appropriate speaking volumes at those times.

On a main screen 1001, pressing a "Scheduling" button takes the user to a Select Week screen 1002. The Select Week screen 1002 shows that two weeks named "Standard" and "Always On" have already been created. For this example, pressing a "New Custom Week" button takes the user to a week configuration screen 1003. In this example, the week name has already been edited to "School." Selection wheels next to each day of the week can allow selection of existing "Weekend" or "Weekday" schedules or creation of a "New Custom Day." Pressing a calendar edit icon next to a "New Custom Day" button opens a day editing screen 1004. As shown, the name of the day has already been edited to "School A." The default time setting for a new day can be a single time window with a start time of 7:00 AM, an end time of 9:00 PM, and a monitor setting of "Too Loud" with a threshold of 85 dB.

Pressing the calendar edit icon next to the time on the day editing screen 1004 advances the user to a threshold time editing screen 1005, which can include selection wheels for start time, end time, lower threshold and upper threshold. After changing the end time to "8:15 AM" and the upper limit to "None," an updated time editing screen 1006 appears. Pressing a "Save" button on the time editing screen 1006 commits the changes and returns the user to an updated day editing screen 1007 showing new parameters compared to the day editing screen 1004. This example demonstrates the ability to explicitly define "Off" times when the monitor 100a does not actively monitor voice volume. Alternatively, any times that are not explicitly defined as having a threshold can be established to be off. During schedule entry, the user interface software 1000 can perform data qualification and can notify the user if one or more inconsistences are detected. As examples of such inconsistencies, if the end time is before the start time, or if the time window overlaps with a previously defined time window, such inconsistencies can trigger a user notification.

A new time window can be generated from the day editing screen 1007 such as by pressing a "+" button. This can take the user to a new time editing screen 1008, such as with the start time defaulting to the end time of the previous time window. In this example, the selection wheels have been adjusted to set the end time to "9:00 AM" and the upper limit to "85 dB," and pressing the "Save" button returns the user to an updated day editing screen 1009. After additional rounds of day editing and time editing, a day editing screen 1010 appears. Pressing a "Done" button returns the user to a week configuration screen 1011. The example screens herein show that all the weekdays are now configured to use the newly created "School A" day, and the weekends are configured to use the pre-existing "Weekend" day. Pressing a "Done" button on the week configuration screen 1011 returns the user to an updated Select Week screen 1012. The Select Week screen 1012 now offers the option to select the newly created "School" week. The customized schedule can then be transferred to the monitor 100*a* by connecting the smart phone 300 to the monitor 100*a* and pressing a "Set Device Schedule" button.

Figure 22:
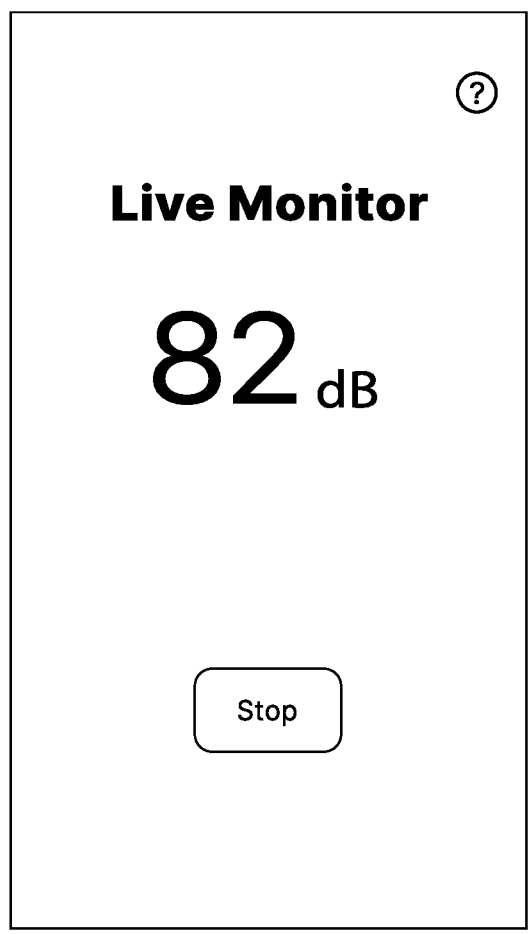
FIG. 22 depicts a wireframe of a screen displayed on a smart phone when live volume monitoring of an exemplary wearable voice volume monitor is occurring.

FIG. 22 depicts an example of a wireframe of a smart phone screen when the live monitoring feature is being utilized. The level of the sound received by the monitor 100*a* is reported on a screen 1013 of the smart phone 300. This feature allows the monitor 100*a* to be worn as it would be normally, while monitoring of the voice level of the wearer is conducted by the wearer or another person having the smart phone 300. By using the live monitoring feature to observe the numeric level associated with speech that is subjectively too loud or too quiet, appropriate threshold levels can be quickly established.

To recap, the present wearable voice volume monitor has the microphone and all the electronics mounted within a small, discreet enclosure, which can be hung from, say, a necklace chain or affixed to clothing such that it appears to be a piece of jewelry. The jewelry appearance is changeable to suit a wearer's personal tastes or current whims, simply by selecting any desired one of a range of different removable decorative pieces that can be made available for users.

While the foregoing written description of exemplary and preferred embodiments enables one of ordinary skill in the art to make and use the present invention, those of ordinary skill will understand and appreciate the existence of variations, combinations and equivalents of the specific embodiments, systems, methods and examples herein. Accordingly, the present invention should not be limited by the described embodiments, systems, methods and examples herein.

The invention claimed is:

1. A voice monitoring system comprising:
a wearable device comprising:
a sound transducer, to receive sound from a user wearing the device to be transduced into an electrical sound signal;
onboard controller circuitry, coupled to the sound transducer to receive and signal-process the electrical sound signal to generate an alert indication in response to a determination that a voice of the user wearing the device meets one or more sound criteria;
a vibration transducer, coupled to the onboard controller circuitry and configured to provide a vibratory alert to the user wearing the wearable device, without requiring a graphical user interface on the wearable device, in response to the alert indication received from the onboard controller circuitry;
onboard communications interface circuitry, coupled to the onboard controller circuitry and configured to communicate with a separate local or remote auxiliary device; and
at least one first receiving fixture configured to receive a user-attachable and user-detachable decorative piece;
the auxiliary device comprising a handheld portable user interface, separate from the wearable device and comprising:
a graphical user interface (GUI) or other human interface device for use by the user of the wearable device or a caregiver;
auxiliary device controller circuitry, coupled to the GUI to receive input to generate a schedule for the one or more sound criteria based on at least one of a time-of-day or day-of-week schedule of the user; and
an auxiliary device communications interface, configured to communicate with the onboard communications interface circuitry of the wearable device for programming the generated schedule for the one or more sound criteria.

2. The voice monitoring system of claim 1, wherein the onboard controller circuitry is configured to at least one of generate or adjust the one or more sound criteria comprising or using at least one of a voice volume level, a voice frequency, a voice nasality, or keyword recognition.

3. The voice monitoring system of claim 1, wherein the wearable device further comprises nonvolatile memory configured to store timestamped records of voice volume levels.

4. The voice monitoring system of claim 1, further comprising at least one second receiving fixture, configured to receive a user-attachable and user-detachable pendant bail for hanging the wearable device therefrom via a flexible strand.

5. The voice monitoring system of claim 1, further comprising a magnetic or magnetizable element configured to user-attach the wearable device to jewelry, a garment, or other accessory worn by the user.

6. The voice monitoring system of claim 1, wherein the wearable device further comprises a screenless user input device comprising at least one of:
an accelerometer configured to sense vibrations to receive user input via tapping on the wearable device;
a button, configured to sense button presses to receive user input; and
a flexing portion of a housing carrying electronic components, the flexing portion configured to sense user input via flexing of the flexing portion of the housing; and
wherein the screenless user input device is configured to receive the user input to at least one of enable or disable at least one of sound monitoring or communication to the auxiliary device via the onboard communication circuitry of the wearable device.

7. The voice monitoring system of claim 1, further comprising the decorative piece, wherein the decorative piece comprises at least one prong, the first receiving fixture comprises at least one receptacle in a housing carrying electronic components, and the at least one prong is user-detachably engageable in said at least one receptacle to attach the decorative piece to the housing.

8. The voice monitoring system of claim 1, further comprising at least one O-ring sized and shaped and otherwise configured to interference fit the decorative piece to the at least one first receiving fixture.

9. The voice monitoring system of claim 1, wherein the onboard controller circuitry is coupled to the sound transducer to receive and signal-process the electrical sound signal to generate an alert indication in response to a determination that a voice of the user wearing the device meets one or more sound criteria including at least one of:
a voice maximum volume threshold; or
a range between a noise floor threshold and a voice minimum volume threshold.

10. The voice monitoring system of claim 1, wherein the wearable device includes a housing comprising a hydrodipped-printed surface texture.

11. A voice monitoring system comprising:
a screenless wearable device comprising:
a sound transducer, to receive sound from a user wearing the wearable device and to transduce the received sound into an electrical sound signal;

onboard controller circuitry, coupled to the sound transducer to receive and signal-process the electrical sound signal to generate an alert indication in response to a determination that a voice of the user wearing the wearable device meets one or more sound criteria during at least one of a specified time-of-day or a specified day-of-week established by a specified voice monitoring schedule;

a vibration transducer, coupled to the onboard controller circuitry and configured to provide a vibratory alert to the user wearing the wearable device in response to the alert indication received from the onboard controller circuitry;

onboard communications interface circuitry, coupled to the onboard controller circuitry and configured to communicate with a separate local or remote auxiliary device; and a fastener, sized and shaped or otherwise configured to fasten the wearable device to the user.

12. The voice monitoring system of claim 11, in which the fastener comprises at least one of a clip, a pin, a pendant bail, a magnet, or a ferromagnetic material.

13. The voice monitoring system of claim 11, in which the wearable device includes at least one first receiving fixture configured to receive a user-attachable and user-detachable decorative piece.

14. The voice monitoring system of claim 11, further comprising:

the auxiliary device, comprising a handheld portable user interface auxiliary device, separate from the wearable device and comprising:

a graphical user interface (GUI) or other human interface device for use by the user of the wearable device or a caregiver;

auxiliary device controller circuitry, coupled to the GUI to receive input to generate a schedule for the at least one sound criteria including a volume criteria based on least one of a time-of-day or day-of-week schedule of the user; and an auxiliary device communications interface, configured to communicate with the onboard communications interface circuitry of the wearable device for programming the generated schedule for the one or more sound criteria.

15. A voice monitoring system comprising:

a screenless wearable device, the wearable device comprising:

a sound transducer, to receive sound from a user wearing the wearable device and to transduce the sound into an electrical sound signal, wherein the sound transducer comprises a wake-on-sound microphone comprising a normal operating mode and a lower-power sleep mode, wherein the microphone, in response to a received sound at a level exceeding a predetermined wakeup threshold during the sleep mode, generates a wake output;

onboard controller circuitry comprising:

a normal operating mode, a lower-power sleep mode, and a mode-switch input coupled to the wake output of the microphone; and wherein the onboard controller circuitry is configured to transition into the normal operating mode upon receiving the wake output at the mode-switch input of the onboard controller circuitry;

wherein the onboard controller circuitry, is configured to receive and signal-process the electrical sound signal to generate an alert indication in response to a determination that a voice of the user wearing the device meets one or more sound criteria;

a vibration transducer, coupled to the onboard controller circuitry and configured to provide a vibratory alert to the user wearing the wearable device, in response to the alert indication received from the onboard controller circuitry;

onboard communications interface circuitry, coupled to the onboard controller circuitry and configured to communicate with a separate local or remote auxiliary device; and at least one of: (1) at least one first receiving fixture configured to receive a user-attachable and user-detachable decorative piece or (2) at least one second receiving fixture configured to receive a user-attachable and user-detachable pendant bail for hanging the wearable device therefrom via a flexible strand; and the separate local or remote auxiliary device, comprising a handheld portable user interface auxiliary device, separate from the wearable device, the handheld portable user interface device comprising:

a graphical user interface (GUI) or other human interface device for use by the user of the wearable device or a caregiver;

auxiliary device controller circuitry, coupled to the GUI to receive input to generate a schedule for the one or more sound criteria based on least one of a time-of-day or day-of-week schedule of the user; and an auxiliary device communications interface, configured to communicate with the onboard communications interface circuitry of the wearable device for programming the generated schedule for the one or more sound criteria without requiring a graphical user interface on the wearable device.

16. The voice monitoring system of claim 15, wherein the wearable device further comprises:

a logarithmic amplitude conversion circuit, comprising a normal operating mode and a lower-power sleep mode, the normal operating mode triggered in response to the wake output of the microphone to enable the logarithmic amplitude conversion circuit to generate a logarithmic signal based upon the electrical sound signal.

17. The voice monitoring system of claim 15, wherein the onboard controller circuitry includes stored instructions that are executable by the onboard controller circuitry to:

wake from the lower power sleep mode into the normal operating mode in response to receiving the wake output from the microphone;

analyze signal information from the electrical sound signal to determine whether a voice of the user wearing the screenless wearable device meets one or more sound criteria using at least one of an amplitude, duration, or persistence characteristic; and actuate the vibration transducer to generate the vibratory alert in response to determining that the voice of the user wearing the device meets one or more sound criteria.

18. The voice monitoring system of claim 15, wherein the onboard controller circuitry includes stored instructions that are executable by the onboard controller circuitry to change one or more of the sound criteria based on least one of a time-of-day or day-of-week schedule of the user.

19. The voice monitoring system of claim 15, wherein the wearable device includes a housing carrying electronic components therein, the housing comprising at least one of the first receiving fixture or the second receiving fixture.

20. The voice monitoring system of claim 15, wherein the handheld portable user interface auxiliary device, separate from the wearable device, includes a smart phone including a display and a touchscreen.

21. The voice monitoring system of claim 15, further comprising the user-attachable and user-detachable decorative piece.

22. The voice monitoring system of claim 15, the wearable device further comprising a magnetic or magnetizable element configured to user-attach the wearable device to jewelry, a garment, or other accessory worn by the user.

23. The voice monitoring system of claim 15, including the at least one second receiving fixture configured to receive a user-attachable and user-detachable pendant bail for hanging the wearable device therefrom via a flexible strand, wherein the second receiving fixture comprises an enclosure comprising a bail post situated within a bail post socket, and further comprising the pendant bail.

24. The voice monitoring system of claim 23, wherein the pendant bail comprises:

first and second bail portions arranged to enter the bail post socket at an entry rotation orientation and to wrap around the bail post when rotated to a retention rotation orientation and to engage each other via at least one of a protrusion and hole, a ball and detent, or an adhesive.

25. The voice monitoring system of claim 23, wherein the pendant bail and the bail post socket are configured for engagement with each other via at least one of a resilient deformation bias, a snap-fit, or a spring bias.

26. A method of voice monitoring, comprising:

receiving user input via a computing device with a graphical user interface to schedule one or more voice monitoring criteria based on at least one of time-of-day or day-of-week to generate a voice monitoring criteria schedule;

transmitting the generated voice monitoring criteria schedule to a screenless voice monitoring wearable device;

changing one or more voice monitoring criteria used by the wearable device based on the generated voice monitoring criteria schedule received from said computing device;

measuring a voice characteristic of a user wearing the wearable device; and alerting the user when the measured voice characteristic meets one or more voice monitoring criteria specified in the generated voice monitoring criteria schedule.

27. The method of claim 26, wherein the voice characteristic is voice volume, and the one or more voice monitoring criteria includes a voice volume threshold, according to the generated voice monitoring criteria schedule to which the voice volume is compared.

28. The method of claim 26, comprising generating a wake signal when a sound detected by the wearable device exceeds a normal operating mode turn-on threshold and, in response to the wake signal, activating a logarithmic amplifier and signal processing of sound detected by the wearable device.

29. The method of claim 26, comprising audibly alerting the user of a location of the wearable device in response to the wearable device being placed into a locator mode via at least one of the computing device or a voice-command received by a sound transducer at the wearable device and recognized as a locator keyword.

* * * * *